US009788756B2

(12) United States Patent
Demmer

(10) Patent No.: US 9,788,756 B2
(45) Date of Patent: Oct. 17, 2017

(54) SYSTEMS, DEVICES, METHODS, AND COMPUTER-READABLE STORAGE FACILITATING LOCATING AN IMPLANTABLE MEDICAL DEVICE WITHIN A BODY

(71) Applicant: Medtronic, Inc., Minneapolis, MN (US)

(72) Inventor: Wade M. Demmer, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 239 days.

(21) Appl. No.: 14/691,036

(22) Filed: Apr. 20, 2015

(65) Prior Publication Data

US 2016/0302692 A1 Oct. 20, 2016

(51) Int. Cl.
| | | |
|---|---|---|
| A61N 1/00 | (2006.01) | |
| A61B 5/06 | (2006.01) | |
| A61N 1/37 | (2006.01) | |
| A61B 5/00 | (2006.01) | |
| A61N 1/372 | (2006.01) | |

(52) U.S. Cl.
CPC ............ *A61B 5/061* (2013.01); *A61B 5/0031* (2013.01); *A61B 5/6898* (2013.01); *A61N 1/37* (2013.01); *A61N 1/37211* (2013.01); *A61N 1/37235* (2013.01); *A61N 1/37247* (2013.01); *A61B 5/062* (2013.01)

(58) Field of Classification Search
CPC ..... A61B 5/061; A61B 5/0031; A61B 5/6898; A61N 1/37; A61N 1/37211; A61N 1/37235; A61N 1/37247
See application file for complete search history.

(56) References Cited

U.S. PATENT DOCUMENTS

| | | |
|---|---|---|
| 4,804,054 A | 2/1989 | Howson et al. |
| 5,107,833 A | 4/1992 | Barsness |
| 5,171,228 A | 12/1992 | McDonald |
| 6,088,619 A | 7/2000 | Hein et al. |

(Continued)

OTHER PUBLICATIONS (PCT/US2016/02823) PCT Notification of Transmittal of the International Search Report and the Written Opinion of the International Searching Authority, Mailed Aug. 1, 2016, 10 pages.

*Primary Examiner* — Scott Getzow

(57) ABSTRACT

Techniques facilitating locating an implantable medical device (IMD) within a body of a patient are provided. An estimate of the location is determined based on strength information representative of strengths of communicative couplings between a communications head device and the IMD at various positions of the communications head device. The strength information can be updated periodically or based on specific events, such as changes to the body and/or an amount of time elapsed since strength information was previously obtained. Media representative of the estimate of the location and an image of the body can be output and can facilitate a patient or caregiver locating the IMD. In some embodiments, the media and image output can guide future placement of the communications head device on the patient to efficiently establish communication. Further, in some embodiments, numerous IMDs implanted within a single body can be identified and communication can commence.

30 Claims, 19 Drawing Sheets

(56) References Cited

U.S. PATENT DOCUMENTS

| | | |
|---|---|---|
| 6,305,381 B1 | 10/2001 | Weijand et al. |
| 6,644,321 B1 | 11/2003 | Behm |
| 6,704,600 B2 | 3/2004 | Daum |
| 6,752,155 B2 | 6/2004 | Behm |
| 7,174,201 B2 | 2/2007 | Govari et al. |
| 7,699,060 B2 | 4/2010 | Behm |
| 7,774,069 B2 | 8/2010 | Olson et al. |
| 7,780,590 B2 | 8/2010 | Birk et al. |
| 7,934,508 B2 | 5/2011 | Behm |
| 8,015,977 B2 | 9/2011 | Bertrand et al. |
| 8,186,358 B2 | 5/2012 | Crivelli et al. |
| 8,192,398 B2 | 6/2012 | Hoendervoogt et al. |
| 8,208,989 B2 | 6/2012 | Maschke et al. |
| 8,509,909 B2 | 8/2013 | Figueiredo et al. |
| 2003/0060859 A1 | 3/2003 | Bourget |
| 2006/0016452 A1 | 1/2006 | Goetz et al. |
| 2007/0279237 A1 | 12/2007 | Julian et al. |
| 2014/0067014 A1 | 3/2014 | Kaula et al. |

SYSTEMS, DEVICES, METHODS, AND COMPUTER-READABLE STORAGE FACILITATING LOCATING AN IMPLANTABLE MEDICAL DEVICE WITHIN A BODY

TECHNICAL FIELD

This disclosure relates generally to implantable devices and, more particularly, to systems, apparatus, methods and computer-readable storage media that facilitate locating an implantable medical device within a body.

BACKGROUND

Contemporary healthcare relies heavily on implantable medical devices (IMDs) to assist patients in leading healthy lives. For example, IMDs such as pacemakers, implantable cardiac defibrillators (ICDs), cardiac resynchronization therapy (CRT) devices, drug delivery systems, and neurostimulators can help manage a broad range of ailments, such as cardiac arrhythmia, diabetes, Parkinson's disease, and the like. Modern IMDs are entrusted with vital tasks in terms of medical care and related therapies, such as delivering insulin or painkillers at proper rates, measuring and collecting biometric data and relaying the data to doctors and/or nurses and/or stimulation of a critical function of an organ, as is the case with cardiac pacemakers, ICDs, CRTs, and neurostimulators.

A patient can benefit from being enrolled in a patient management system that can utilize information collected by IMDs to assess wellbeing of the patient, adjust existing therapies, predict impending episodes or the development of comorbidities, monitor operation of the IMD, and the like. As such, access to such a system can enhance the prospects of successfully managing a health condition for which the IMD is implanted. To access the IMD, a telemetry device must typically be located in close proximity to the IMD. Yet, in some cases, due to small size of an IMD or due to particular shape of an IMD, a morphological landmark of the IMD may not be readily available or accessible on the body of the patient. Accordingly, identification of a suitable location for placement of a telemetry device for communication with and/or collection of information from the IMD may be difficult. Accordingly, there is a business desire for approaches that facilitate locating an IMD within the body of the patient.

SUMMARY

The following presents a simplified summary in order to provide a basic understanding of one or more of the embodiments. This summary is not an extensive overview of the embodiments described herein. It is intended to neither identify key or critical elements of the embodiments nor delineate any scope of embodiments or the claims. Its sole purpose is to present some concepts of the embodiments in a simplified form as a prelude to the more detailed description that is presented later. It will also be appreciated that the detailed description may include additional or alternative embodiments beyond those described in the Summary section.

Embodiments described herein include systems, apparatus, methods and computer-readable storage media that facilitate locating an implantable device within a body. In one embodiment, a device includes a memory that stores executable modules, and a processor coupled to the memory and configured to execute at least some of the executable modules stored in the memory. The device can be embodied in or can include at least one of a tablet computer or a smart phone. The executable modules can include a map composition module configured to generate information indicative of a first electronic map, wherein the first electronic map is representative of respective strengths of communicative couplings between a communications head device and an IMD within a body at multiple positions of the communications head device relative to the body and at a first defined time period. In certain implementations, the map composition module can be further configured to generate information indicative of a second electronic map, wherein the second electronic map is representative of respective strengths of communicative couplings between the communications head device and the IMD within the body at multiple second locations of the communications head device relative to the body and at a second defined time period. In other implementations, the map composition module is further configured to generate the information indicative of the second electronic map based on a change in size of the body, a time interval that has elapsed between commencement of the first defined time period and commencement of the second defined time period, or a defined change in a strength of a communicative coupling at a defined location of the body relative to an initial strength of an initial communicative coupling at the defined location of the body as indicated in the first electronic map.

The executable modules also can include a location prediction module configured to estimate an implant location of the IMD within the body based on the information indicative of the first electronic map. In one implementation, the location prediction module can be further configured to determine a location within the first electronic map at which one of the strengths of the communicative couplings is indicative of strength intensity greater than a defined threshold.

In another implementation, the location prediction module can be further configured to predict a location within the first electronic map at which one of the strengths of the communicative couplings is indicative of maximal strength intensity. In yet another implementation, the location prediction module is further configured to determine that the IMD is located at a second implant location, and the map composition module is further configured to generate the information indicative of the second electronic map based on a determination that the IMD is located at the second implant location.

In addition, the executable modules can include a media composition module configured to generate imaging information representative of the estimated implant location and at least a portion of the body. The device also can include a display device configured to display indicia representative of at least a portion of the imaging information. In one example, the indicia can include media including one or more of a video segment, a photograph, or schematic image. The display device can be further configured to display a prompt to place the communications head device in a defined position relative to the body.

Further, the executable modules can include an acquisition module configured to receive strength data indicative of respective strength of signals received by the communications head device from the IMD at multiple locations along a path within the area, and wherein the processor is further configured to execute the acquisition module. In one implementation, the acquisition module can be further configured to receive second imaging information representative of respective images of the communications head device at the multiple locations. In such an implementation, the map composition module can be further configured to match portions of the strength data to respective locations of the multiple locations. In addition, the device further comprises a camera that images the communications head device and at least a portion of the body, and generates the second imaging information.

In another embodiment, a device includes a display device configured to output first indicia representative of a location of an IMD within an area of a body, wherein the location is determined based on information indicative of a map representative of respective strengths of communicative couplings between a communications head device and the IMD at multiple positions of the communications head device. The device can also include a memory that stores executable modules and a processor coupled to the memory and configured to execute a placement monitor module configured to determine whether the placement of the communications head device satisfies a coupling criterion between the communications head device and the IMD. In one implementation, the placement monitor module can be further configured to cause the device to transmit, to the communications head device, a signal to cause the communications head device to output a haptic signal or an audio output signal if the placement of the communications head device satisfies the coupling criterion.

In another implementation, the placement monitor module is further configured to process at least one of first data or second data from the communications head device, wherein the first data comprises strength data representative of a strength of a signal received from the IMD by the communications head device at a defined location, and wherein the second data comprises raw data received from the IMD by the communications head device at the defined location.

In another embodiment, a computer-readable storage device is provided. The computer-readable storage device stores instructions that, in response to execution, cause a device including a processor to perform operations. The operations include: generating information representative of respective strengths of communicative couplings between a communications head device and an IMD within a body at multiple positions of the communications head device; determining an estimate of a location of the IMD within the body based at least on the information; and generating imaging information representative of the estimate of the location and at least a portion of the body. In one implementation, the determining can include predicting a position associated with a portion of the information representative of maximal strength intensity. The operations also can include causing the device to display a visual representation of at least a portion of the imaging information.

In yet another embodiment, another computer-readable storage device is provided. The computer-readable storage device stores instructions that, in response to execution, cause a device including a processor to perform operations. The operations include: displaying first indicia representative of a location of an IMD within an area of a body, wherein the location is determined based on information indicative of a map representative of respective strengths of communicative couplings between a communications head device and the IMD at one or more positions of the communications head device; determining that placement of the communications head device satisfies a coupling criterion between the communications head device and the IMD; and in response to the determining, outputting a first indication that the placement of the communications head device satisfies the coupling criterion.

In one example, the first indication includes at least one of an audio output signal, a haptic signal, or a video output signal indicative of a second indicia representative of the location of the IMD. In addition, the operations can further include causing the device to transmit, to the communications head device, a signal to output a second indication that the placement of the communications head device satisfies the coupling criterion.

In still another embodiment, a method is provided. The method can include: generating, by a device including a processor, information representative of respective strengths of communicative couplings between a communications head device and an IMD within a body at multiple positions of the communications head device. In addition, the method can include determining, by the device, an implant location of the IMD based at least on the information; and generating, by the device, imaging information representative of the implant location and at least a portion of the body. In one implementation, the determining can include determining a location associated with strength intensity represented by a portion of the information that satisfies a defined criterion. In another implementation, the determining includes predicting a position associated with a portion of the information representative of maximal strength intensity. The method can also include displaying a visual representation of at least a portion of the imaging information.

In yet another embodiment, a method is provided. The method includes presenting, by a device including a processor, indicia representative of a location of an IMD within an area of a body, wherein the location is determined from a map representative of strength of a communicative coupling between a communications head device and the IMD as a function of position within the area. The method also includes determining, by the device, that placement of the communications head device satisfies coupling criterion between the communications head device and the IMD. In addition, the method includes, in response to the determining, providing, by the device, an indication that the placement of the communications head device satisfies the coupling criterion. In one implementation, the providing can include one or more of outputting an audio signal, outputting a haptic signal, outputting a video output signal, or replacing the indicia with updated indicia representative of the location of the IMD. In another implementation, the providing comprises sending an instruction to the communications head device to output one or more of a haptic signal or an audio signal. In some embodiments, the method also includes, prior to the determining, presenting, by the device, a prompt to place the communications head device in proximity to the location of the IMD.

In another embodiment, another method is provided. The method includes determining, by a device including a processor, a location of an IMD within a patient based at least on information associated with the patient and a current location of the IMD, wherein the current location is determined from a map representative of strength of a communicative coupling between a communications head device and the IMD as a function of position of the communications head device; and determining that a difference between the location and the current location is greater than a defined threshold. The method can also include presenting a prompt to update location information representative of the current location based on the determining.

In still another embodiment, another method is provided. The method includes: collecting, by a device including a processor, information representative of respective strengths of communicative couplings between a communications head device and an implantable device at multiple positions of the communications head device relative to a body in which the implantable device is implanted. The method can also include: generating an estimate of the location of the implantable device within the body based at least on the information; displaying a prompt to place the communications head device in proximity of the implantable device within the body and media representative of the estimate of the location of the implantable device; and outputting an indication that placement of the communications head device satisfies a placement criterion, wherein the indication comprises at least one of an audio output signal, a video output signal, or a haptic signal.

In one embodiment, a system is provided. The system can include: a communications head device configured to determine strength data indicative of communicative couplings between the communications head device and an IMD located within a body of a patient. The system can also include a device communicatively coupled to the communications head device and configured to: receive the strength data; generate an electronic map based on the strength data; determine an estimate of the location of the IMD within the body based at least on the electronic map; and display media representative of the estimate of the location of the IMD.

In certain implementations, the device can be further configured to display a prompt to instruct a user of the communications head device to place the communications head device in proximity of the IMD.

In other implementations, the device can be further configured to output an indication that placement of the communications head device satisfies a placement criterion, wherein the indication comprises at least one of an audio output signal, a video output signal, or a haptic signal. In the system, in one implementation, the IMD can be configured to exchange information with the communications head device to determine at least a portion of the strength data. The system also can include a server device communicatively coupled to the device and configured to at least one of store information about the patient or transmit information about the patient to the device. In some implementations, the device can be further configured to obtain new strength data from the communications head device and generate a new electronic map based on information about the patient.

In another embodiment, another system is provided. The system can include: a communications head device configured to determine strength data indicative of communicative couplings between the communications head device and one or more IMDs located within a body of a patient. The system can also include a device communicatively coupled to the communications head device and configured to: receive the strength data for the one or more implantable medical devices; and generate one or more respective electronic maps based on the strength data for the one or more implantable medical devices, wherein a first electronic map of the one or more respective electronic maps is associated with a first implantable medical device of the implantable medical devices and wherein a second electronic map of the one or more respective electronic maps is associated with a second implantable medical device of the implantable medical devices. The device can also be configured to: determine estimates of one or more respective locations of the one or more implantable medical devices within the body based at least on the one or more respective electronic maps; and display media representative of the estimates of the one or more respective locations of the one or more implantable medical devices.

In certain implementations, the device is also configured to display a prompt to instruct a user of the communications head device to place the communications head device in proximity of the first implantable medical device, the second implantable medical device or an overlap region associated with communication between the communications head device, the first implantable medical device and the second implantable medical device. For example, in some embodiments, the communications head device can be placed in a first location to communicate with the first IMD, placed in a second location to communicate with the second IMD or placed in a third location (e.g., an overlap location) to communicate concurrently with the first IMD and the second IMD.

Other embodiments and various non-limiting examples, scenarios and implementations are described in more detail below. The following description and the drawings set forth certain illustrative embodiments of the specification. These embodiments are indicative, however, of but a few of the various ways in which the principles of the specification may be employed. Other advantages and novel features of the embodiments described will become apparent from the following detailed description of the specification when considered in conjunction with the drawings.

DETAILED DESCRIPTION

Figure 1:
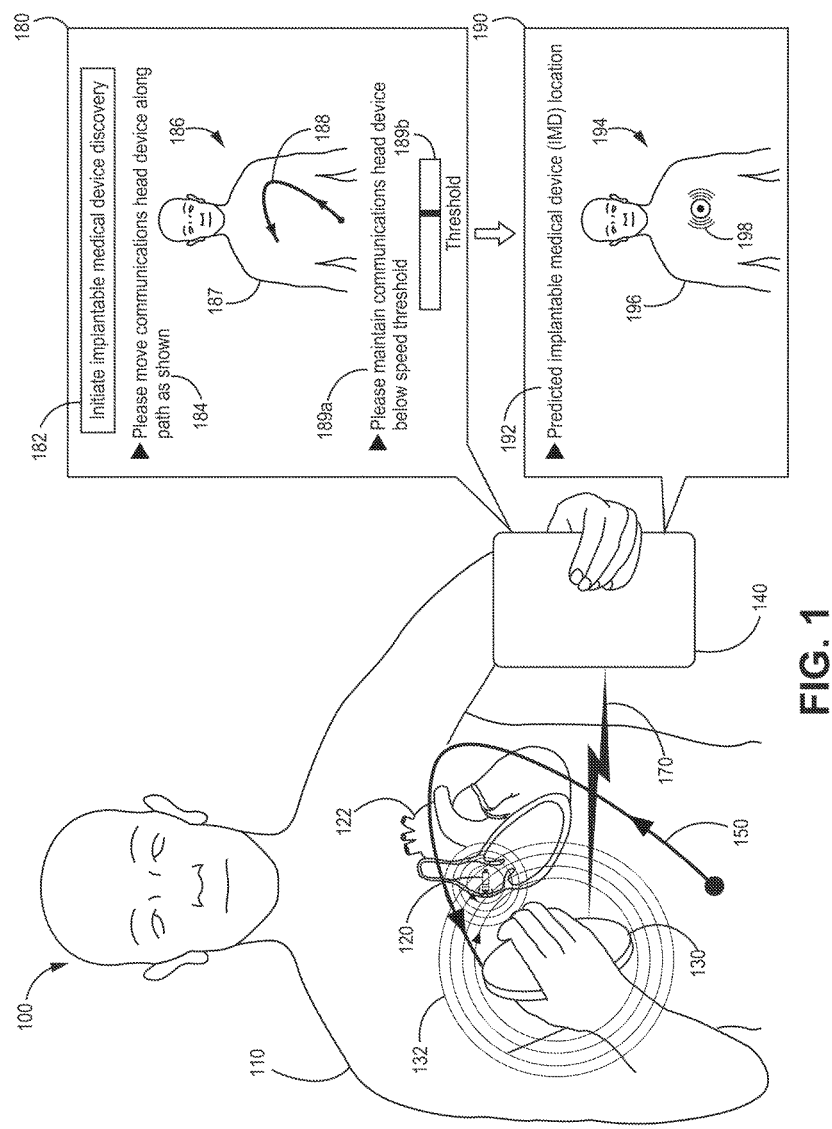
FIGS. 1-2 illustrate schematic diagrams of example, non-limiting medical device locating systems facilitating locating an IMD in accordance with one or more embodiments described herein.

The following detailed description is merely illustrative and is not intended to limit embodiments and/or application or uses of embodiments. Furthermore, there is no intention to be bound by any expressed or implied information presented in the preceding Technical Field, Background or Summary sections, or in the Detailed Description section.

One or more embodiments are now described with reference to the drawings, wherein like reference numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Additionally, the following description refers to components being "connected" and/or "coupled" to one another. As used herein, unless expressly stated otherwise, the terms "connected" and/or "coupled" mean that one component is directly or indirectly connected to another component, mechanically, electrically, wirelessly, inductively or otherwise. Thus, although the figures may depict example arrangements of components, additional and/or intervening components may be present in one or more embodiments.

As employed in this specification and annexed drawings, the terms "component," "module," "unit," "system," "platform," "interface," and the like are intended to refer to a computer-related entity or an entity related to an operational apparatus with one or more specific functionalities, wherein the computer-related entities or entities can be either hardware, a combination of hardware and software, software, or software in execution. As an example, a component can be, but is not limited to being, electronic circuitry, one or more devices, a combination of one or more devices and electronic circuitry, a process running on a processor, a processor, a memory, a code object, an executable code instruction, a thread of execution, a program, and/or a computer. By way of illustration, both an application running on a server device and the server device can be a component. One or more components can reside within a process and/or thread of execution and a component can be localized on one computer and/or distributed between two or more computers. In addition, these components can execute from various computer-readable storage media having various data structures or code instructions stored on the computer-readable storage media. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry. As yet another example, a component can be an apparatus that provides specific functionality through electronic components without mechanical parts. As further yet another example, one or more user interfaces can include one or more input/output (I/O) components and, in some embodiments, associated processor, application, or Application Programming Interface (API) components.

The present disclosure recognizes and addresses, in at least certain embodiments, the issue of discovery of the location of an IMD within a body. Described herein are apparatuses, computer-readable storage devices, systems, and/or methods that facilitate locating or otherwise determination of the placement of an IMD (IMD) within a body. To that end, one or more embodiments leverage an assessment of the communicative coupling between a communications head device and the IMD as a function of position of the communications head device at different areas of the body. In addition, one or more embodiments determine an estimate of the location of the IMD based on such an assessment, and leverage an augmented reality representation of the body in order to convey the estimated location.

It should be appreciated that the assessment of the communicative coupling can include exchange of complex information between electronic devices and, thus, cannot be carried out by a human, and is neither abstract nor a fundamental concept that is merely automated. Therefore, the approaches for locating and/or for discovery of the location an IMD in accordance with the various embodiments described herein also cannot be implemented by a human. It should further be appreciated that the augmented reality representations described herein provide a rich, complex interface that may readily identify the location of the IMD relative to the different locations (e.g., trunk, arms, head) of the body.

As described in greater detail below, in certain embodiments, the placement of an IMD within a body can be determined via a communications head device that can communicate wirelessly with the IMD and a remote computing device. Specifically, yet not exclusively, the communications head device can be moved in a path within an area in which the IMD may be implanted, and for each (or, in some embodiments, one or more) of multiple locations along the path, the communications head device can determine strength information representative of a communicative coupling between the communications head device and the IMD. The communicative coupling can be specific to the architecture of the communications head device and the IMD, and can include inductive coupling and/or radio frequency (RF) coupling. In one example, the strength information can include strength data and/or strength metadata representative of the communicative coupling. In some embodiments, the strength information can include a device identification (ID) indicative of the IMD associated with the strength information. The IMD can provide the device ID to the communications head device. The device ID can be employed to allow strength information received from one IMD to be distinguished from strength information received from another IMD within the body of the patient. In another example, the strength information can include raw data and/or metadata that can permit, after certain processing, a determination of the communicative coupling. Regardless of the type of the strength information, the remote device can receive at least a portion of the strength information and can generate a strength map representative of the magnitude (or intensity) of the communicative coupling as a function of the position within an area of the body. In addition or in other embodiments, the remote device can determine an estimate of the location of the IMD within the area based at least on the strength map. To that end, in one or more embodiments, the remote device can determine a position within the area at which the strength intensity is maximal. In other embodiments, the remote device can determine a position within the area at which an actual strength magnitude or a predicted strength magnitude is greater than or equal to a defined threshold. Regardless of implementation, the remote device can assign or otherwise associate such an estimate to a location of the IMD within the body. In addition or in other embodiments, the remote device can store in memory (e.g., one or more computer readable storage devices) the estimate of the location of the IMD within the body and at least a portion of the strength information utilized to estimate the location of the IMD. Thus, the remote device can utilize the stored information at a later time without additional collection of strength information and/or without determination of another estimate of the location of the IMD.

In addition to determining location of an IMD within a body based on strength information in accordance with this disclosure, in certain embodiments, the remote device that is communicatively coupled with the communications head device can present or otherwise provide an augmented reality representation of the body and the location of the IMD. Therefore, in one or more of such embodiments, the remote device can generate imaging information representative of the body and the location of the IMD, and can present indicia (or markings) representative of the body and the location of the IMD. In one example, the remote device can leverage or otherwise utilize a camera or other type of input interface to image the body before, during, and/or after the communications head device is moved along a path for collection of strength information. The imaging information generated by the remote device can correspond to at least one of the images collected or otherwise obtained by the camera. The imaging information can correspond to a motion picture or still picture of the communications head device as it traverses the path. A portion of the imaging can be annotated, tagged or otherwise labeled or modified in order to identify a position or orientation of the communications head device relative to the body. An image represented by an image frame in the motion picture can be analyzed to determine or otherwise estimate a position of the communications head device relative to the body. The image frame also can be tagged (e.g., time stamped). The position so determined can be associated with strength information received when the image frame is tagged or labeled. In addition or in other embodiments, an estimate of the speed of the communications head device can be utilized to determine a position of the communications head device relative to the body.

In some embodiments, the time elapsed between successive collection of strength information can be determined by the remote device as the communications head device traverses the path. In addition, the remote device can augment or otherwise supplement such imaging information with other imaging information indicative of the location of the IMD. The remote device can present indicia representative of the imaging information obtained via the camera and other indicia representative of the other imaging information. Thus, it should be appreciated that the location of the IMD can be presented with reference to the body without reliance on a morphological landmark within the body or associated therewith.

It should be appreciated that while various embodiments are described in connection with a single IMD, the embodiments described herein are not limited in this respect and respective strength maps can be generated for any number of IMDs within a single body. Each of the generated strength maps can be utilized to predict or otherwise determine an estimate of the position of a corresponding IMD in accordance with aspects described herein.

With reference to the drawings, FIG. 1 illustrates a schematic diagram of an example, non-limiting medical device locating system 100 facilitating locating an IMD in accordance with one or more embodiments described herein. As illustrated, an IMD 120 can be implanted within a body 110 (such as the body of a patient). In various embodiments, the IMD 120 can be embodied in or can constitute any of a number of different types of IMDs (e.g., leadless pacemaker, ICD, an implantable drug delivery device, a neurostimulator, an implantable monitoring device (such as a cardiac loop recorder, pressure monitor, or the like)). In addition or in other embodiments, the IMD 120 can be implanted within any of various different locations within the body 110 including, but not limited to, the chest region of the body 110 (as shown), the head region of the body 110 or otherwise. Further, while the embodiment of FIG. 1 is shown with reference to the body 110 of a human, in other embodiments, the embodiment can be extended to those in which the IMD 120 is implanted in an animal or any number of different types of living beings. All such embodiments are envisaged.

In the embodiment shown, the IMD 120 is embodied in or can constitute a leadless pacemaker implanted within a chamber, e.g., an atrium or ventricle of a heart 122. In other embodiments, however, IMD 120 can be attached to the outside of the heart 122. The size and/or form factor of the IMD 120 can permit insertion of the IMD 120 into the chamber of the heart 122 in a manner such that the ability for a patient or caregiver to physically detect a morphological landmark (e.g., a protrusion from the skin of the body 110) indicating the location of the IMD 120 can be difficult or altogether impossible. As such, the specific location of the IMD 120 within the body 110 can become unknown after the IMD 120 has been implanted.

A communications head device 130 configured to communicate with the IMD 120 can be placed in proximity to the IMD 120 to receive information associated with operation of the IMD 120 and/or a condition of the body 110. For example, the communications head device 130 can receive from the IMD 120 information indicative of biometric data (e.g., heart rate, blood pressure, etc.) about the body 110 and/or other metrics indicative of a health state of the body 110, such as blood glucose level, cholesterol level, urea levels, neural activity, a combination thereof, or the like. The information can also include data about cardiac or other physiological events experienced by the patient associated with the body 110, electrical stimulation or other therapies provided by or to the patient associated with the body 110, and/or information associated with the performance or longevity of the IMD 120. The communications head device 130 and the IMD 120 can exchange information wirelessly. As such, the communications head device 130 can include components for wireless communication, such as induction coils for inductive coupling, a transmitter, a receiver, or a transceiver. Such components leverage inductive coupling and/or propagation of electromagnetic waves in order to permit communication with the IMD 120.

Upon or after activation of the communications head device 130, a signal can be emitted from the communications head device 130 that can cause the IMD 120 to transition to a fully energized state and/or to activate one or more functions of the IMD 120 that can be employed to facilitate detection of the location of the IMD 120 via placement of the communications head device 130 in one or more locations of the body 110. In some embodiments, however, one or more portions of the IMD 120 can be activated prior to emission of the signal by the communications head device 130. For example, in some embodiments, the IMD 120 can awaken and emit a signal periodically, based on the occurrence of an event or based on any number of different scenarios.

In one embodiment, the IMD 120 and the communications head device 130 can be configured to be inductively coupleable with one another via a magnetic field 132, in response to or based on the presence of the communications head device 130 relative to the IMD 120. For example, in some embodiments, the IMD 120 and the communications head device 130 can each include inductive circuitry (not shown). For example, in some embodiments, the IMD 120 can include a primary coil with a defined number of turns dictated by the desired strength of the magnetic field to be generated by the primary coil. The communications head device 130 can include a secondary coil that can be brought into close proximity (e.g., 2-10 centimeters) of the inductive circuitry of the IMD 120. The IMD 120 and the communications head device 130 can each transmit and receive modulated magnetic fields to communicate with one another. Current flowing through the inductive circuitry can be employed for inductive coupling communication between the IMD 120 and the communications head device 130.

The IMD 120 and the communications head device 130 can exchange information (e.g., data, metadata, and/or signaling) while the IMD 120 and the communications head device 130 are inductively coupled. In some embodiments, the IMD 120 and the communications head device 130 can be configured to communicate via any of a number of communication protocols, including propriety communication protocols and/or non-proprietary communication protocols (e.g., BLUETOOTH® or near field communication (NFC)). In scenarios in which other IMDs besides IMD 120 are implanted in the body 110, the communications head device 130 can communicate according to multiple, different communications protocols in order to exchange information (e.g., data and/or metadata) with each of the IMDs. For instance, the communications head device 130 can communicate inductively with the IMD 120 and via RF waves with another IMD (not shown) within the body 110. As another example, the communications head device 130 can employ a first telemetry protocol (e.g., proprietary or non-proprietary communication protocol) for communication with IMD 120 and employ a second telemetry protocol (e.g., proprietary or non-proprietary communication protocol) for communication with another IMD (not shown) in the body 110.

Accordingly, the communications head device 130 and the IMD 120 can exchange information wirelessly. In some embodiments, the communications head device 130 and the IMD 120 can engage in bidirectional communication with one another. In some embodiments, the IMD 120 can engage in unidirectional communication in which the IMD 120 emits a beacon signal that can be detected by the communications head device 130.

At least a portion of the information received by the communications head device 130 from the IMD 120 can be employed to evaluate and/or determine the strength of the communicative coupling for a specific relative arrangement of the communications head device 130 and the IMD 120. By way of example, but not limitation, the relative arrangement can be or include relative distance between the communications head device 130 and the IMD 120 and/or relative orientation of the communications head device 130 and the IMD 120. For example, in some embodiments, the strength of the signal received by the communications head device 130 when the communications head device 130 is at different positions relative to the IMD 120 is one example of the type of information that can be received by the communications head device 130.

In certain embodiments, the communications head device 130 can generate the strength information and can send at least a portion of the strength information to a device 140. To that end, in one embodiment, the communications head device 130 can measure power of the analog signal received from the IMD 120. Thus, the strength information can be indicative of or otherwise representative of the measured power. In addition, in some embodiments, the strength information can include a device ID indicative of the IMD 120. For instance, the communications head device 130 can augment or otherwise tag the strength information metadata indicative of the device ID. The device ID can be embodied in, for example, an electronic serial number (ESN) and/or can be received from the IMD 120. Device 140 can be located external to the body 110 and communicatively coupleable to the communications head device 130.

As illustrated, in certain embodiments, the device 140 can be communicatively coupled with communications head device 130 via a signal 170. The signal 170 can include, but is not limited to, any number of different types of magnetic or electromagnetic (EM) waves (e.g., RF waves, IR waves, or other types of EM waves). The signal 170 can represent a bidirectional set of wireless links between the communications head device 130 and the device 140.

In one example, to determine a strength of a communicative coupling between the communications head device 130 and the IMD 120, the communications head device 130 or the external device 140 can send (e.g., broadcast), periodically or at certain intervals, a pilot signal intended to cause the IMD 120 to transition from a power-save state to an active state. As such, the pilot signal can be considered to be a wake-up signal. In certain embodiments, the wake-up signal also can cause the IMD 120 to send (e.g., broadcast) a device ID. The device ID can be a unique identifier of the IMD 120 in some embodiments.

In response to detecting the wake-up signal, the IMD 120 can transition from the power-save state to the active state, and can send (e.g., broadcast) another pilot signal (e.g., an ACK signal) indicative of the readiness of the IMD 120 to receive and send information other than pilot signals. In some embodiments, the communications head device 130 can receive the pilot signal from the IMD 120, transmit one or more probe messages to the IMD 120 and monitor a response from the IMD 120 to the one or more probe messages. In one scenario, the IMD 120 can send a response message in response to a probe message. The response message can include payload data indicative of reception of the probe message. In another scenario, the probe message can time out or otherwise be unanswered by the IMD 120.

Therefore, the communications head device 130 can determine the strength of the communicative coupling with the IMD 120 based at least on a group of probe messages and the corresponding response message sent from the IMD 120 (or lack of response message sent) in response to the group of probe messages. In addition to or in the alternative, the communications head device 130 can measure the intensity of signals received from the IMD 120, and can determine the strength of the communicative coupling based at least on the measured intensity.

In other embodiments, the communications head device 130 can send (e.g., broadcast, unicast, or otherwise transmit), to a device 140, unprocessed information (e.g., raw data) representative of an exchange of probe messages and response messages between the communications head device 130 and the IMD 120, or representative of measurements of received signal intensity (e.g., received power) at the communications head device 130. The device 140 can receive at least a portion of the unprocessed information and can determine strength information at different locations of the communications head device 130 relative to the IMD 120 using the received information. The device 140 can be embodied in or can constitute a computing device, such as a smart phone, a tablet computer, mobile device, a blade server or other types of server device, or the like.

As described herein, absence of a morphological landmark (e.g., a protrusion or raised area of skin) associated with the IMD 120 can cause uncertainty regarding placement of the IMD 120 within the body 110 after a certain period since the IMD 120 was implanted. Absence of morphological landmarks can be prevalent in implantable monitoring devices, which may have smaller form factors than implantable devices that provide therapies.

The device 140 can utilize or otherwise leverage the strength information representative of communicative coupling between the communications head device 130 and the IMD 120 at different locations of the communications head device 130 to determine or otherwise identify or estimate the placement of the IMD 120 within the body 110 of the patient. To that end, in certain embodiments, the device 140 can display or otherwise present prompts to instruct the patient or caregiver to move the communications head device 130 at certain speed(s) along a path 150 within an area of the body 110. It should be recognized that the particular geometry of the path 150 is illustrative and that other geometries are contemplated in this disclosure. For example, in some embodiments, in lieu of employing predetermined geometries such as the spiral or Z-shaped geometries, one or more geometries can be dynamically determined based on information received from the IMD 120. For example, information received from the IMD 120 can be utilized to determine the next one or more locations at which the communications head device 130 should be moved relative to the body 110 of the patient.

In certain implementations, the device 140 can display a user interface 180 including selectable indicia 182 prompting the patient or caregiver to initiate IMD discovery. While a specific message is shown in FIG. 1 in connection with the selectable indicia 182, it should be recognized that any message instructing the patient or caregiver to initiate such a discovery can be employed. The device 140 can display the user interface 180 via a display device having a screen. The screen can be or can include a touch screen in some embodiments. However, other types of output interfaces can also be utilized to present the user interface 180 and related indicia. The selectable indicia 182 can be selected via touch (e.g., tap or pressure swipe) or other types of user-interface interactions (e.g., gestures, or utterances or other speech commands, including specific keywords or phrases), activation of a keyboard (not shown) or mouse pad (not shown) or the like.

Selection of the indicia 182 can cause the device 140 to present indicia 184 and indicia 186. As illustrated, the indicia 184 instructs a patient or caregiver to move the communications head device 130 along the path 150, and the indicia 186 can present an image 187 of the body 110 and indicia 188 representative of the path 150. While the indicia 188 prescribes the path 150 in a single rendering, in certain embodiments, a path can be prescribed dynamically, e.g., positions or portions of the path 150 can be presented as a function of time. In one of such embodiments, the device 140 can display the indicia 188 as a function of time, where a subsequent position of the path 150 can be determined by the device 140 in response to strength information (e.g., strength data) received from the communications head device. As such, a prescribed path can guide progressive placement of the communications head device 130 towards regions of higher strength of communicative coupling between the communications head device 130 and the IMD 120, while guiding the placement of the communications head device 130 away from regions of lower strength of communicative coupling.

In some embodiments, selection of the indicia 182 can cause the device 140 to present a prompt and/or related indicia to orient the communications head device 130 in specific directions relative to the body 110. For instance, the indicia can graphically convey certain roll, pitch, and/or yaw information in which the communications head device 130 can then be oriented. It should be appreciated that, for certain communications head devices, orientation information can be particularly pertinent because the construction of such devices can be orientation dependent.

In one example, with further reference to the indicia 186, the image 187 can be embodied as or can include a motion picture (such as video displayed as an animation or a real-time image feed) or a still picture (such as a photograph), and can be acquired by a camera of the device 140, which can process imaging information representative of the acquired image and can present the image 187. In another example, the image 187 can be a graphical representation of a portion of the body 110 and the device 140 can generate imaging information associated with such a representation. For instance, the graphical representation can be schematic, including media that represents the portion of the body as a sketch or an outline. As such, the image can be that of the actual body 110 of the patient or a mere representation of the body 110 of the patient.

In addition, selection of the indicia 182 can cause the device 140 to present indicia 189a prompting the patient or caregiver to maintain the communications head device 130 below a speed threshold during movement along the path 150. The device 140 can also present indicia 189b representative of a current speed of the communications head device 130 and the speed threshold (indicated with a thick line and the label "threshold," although other labels can be employed in other embodiments). The device 140 can determine or otherwise estimate the current speed of the communications head device 130. For example, the device 140 can determine and/or estimate the current speed at which the communications head device 130 is being moved by the patient and/or caregiver based on the frequency with which strength information is being received by the device 140. As another example, the device 140 can leverage a camera to acquire imaging information indicative or otherwise representative of one or more positions of the communications head device 130 along the path 150, and can process the imaging information to determine distances between successive positions. In addition, the device 140 can leverage an internal clock to determine the time elapsed between successive positions and, in combination with the determined distances, estimate the current speed of movement of the communications head device 130. In yet another example, the speed of movement of the communications head device 130 can be determined or deduced based on the operation of a sensor (not shown). For example, device 140 can receive an estimate of the current speed of the communications head device 130 from a sensor (such as an accelerometer or other circuitry configured to facilitate detection of speed of movement of the communications head device 130). In one or more embodiments, the sensor can be located in the communications head device 130.

As described in greater detail below, after the communications head device 130 has traversed a prescribed path, such as path 150, the device 140 can present a user interface 190 including indicia 192 that introduces a predicted location of the IMD 120. The user interface 190 can also include indicia 194, which can be a display of a combination of an image 196 of a portion of the body 110 and indicia 198 that visually conveys the position of the IMD 120 relative to the imaged portion of the body 110. In one embodiment, the indicia 194 can display or represent a motion picture of the body 110. In one embodiment, the indicia 198 displayed can be updated according to the movement of the body 110. Other indicia besides the indicia 198 shown can be presented in other embodiments towards providing a detailed view of the body 110 and/or the location of the IMD 120 within the body 110.

Figure 7:
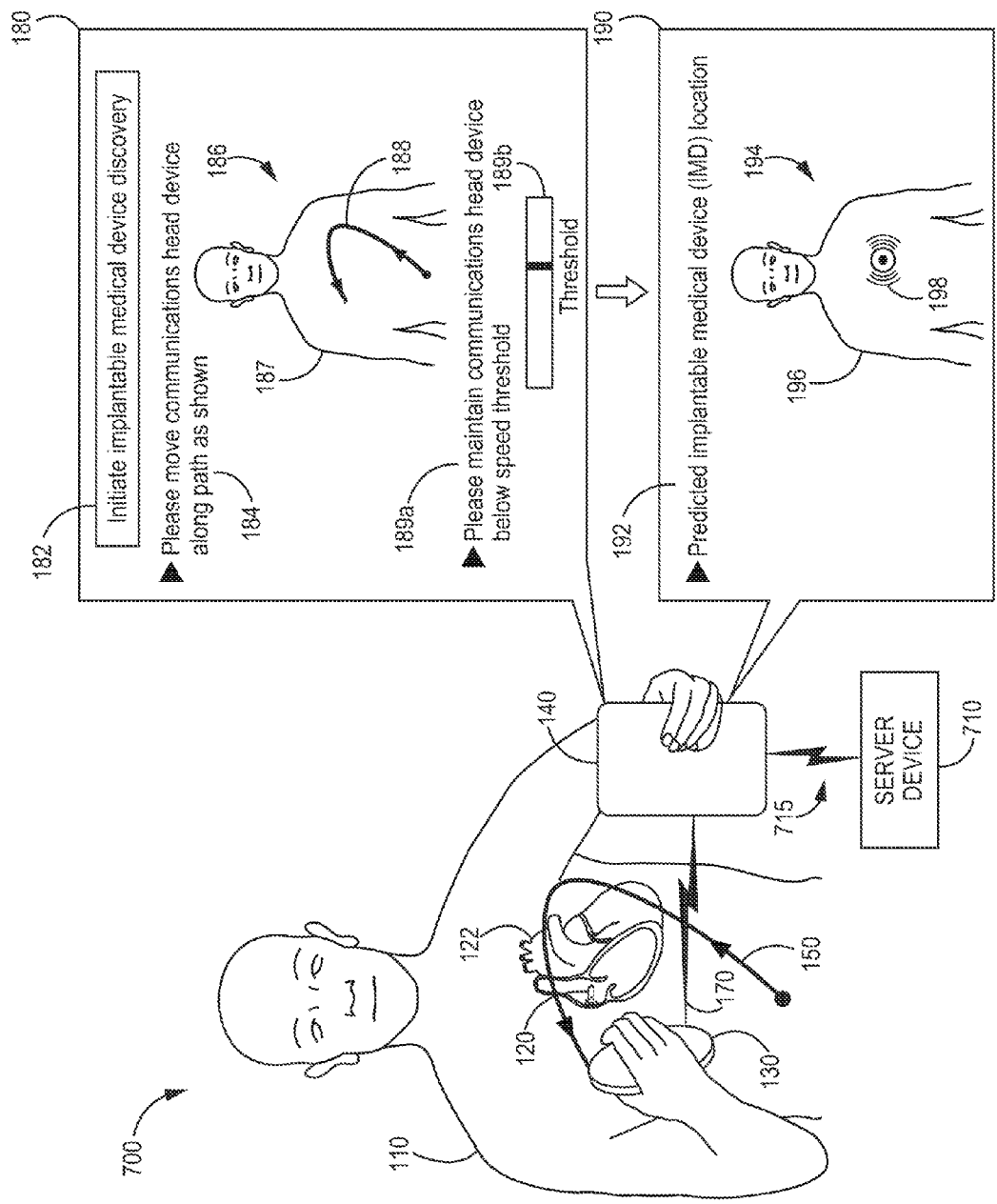
FIGS. 7-8 illustrate schematic diagrams of example, non-limiting medical device locating systems facilitating locating an IMD in accordance with one or more embodiments described herein.
Figure 8:
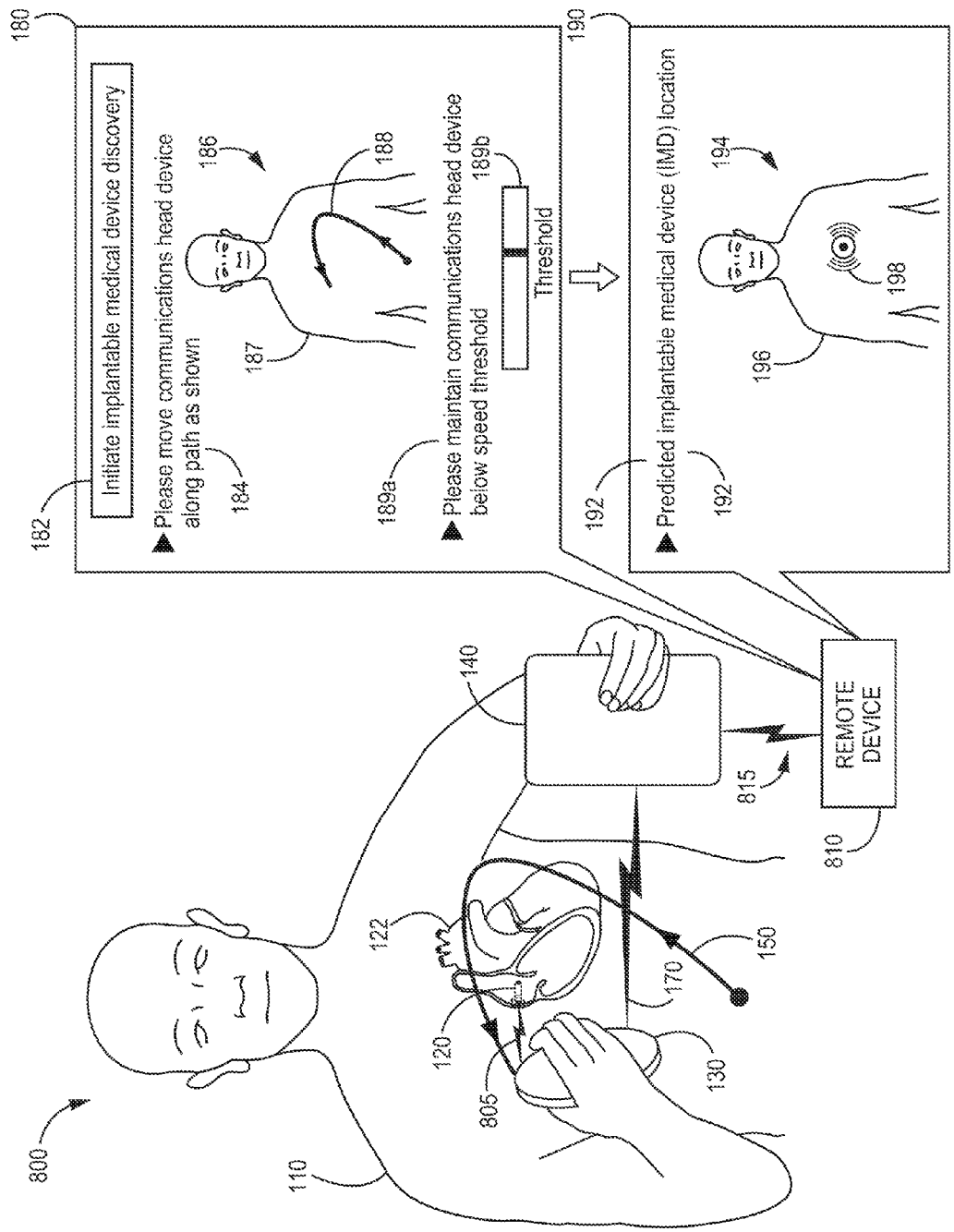

In some embodiments, indicia 198, indicia 194 and/or other information indicative of or employed to facilitate display of the location of the IMD 120 within the body 110 and/or shown as part of user interface 190 can be information stored in the device 140 (or in server device 710 of FIG. 7 or in remote device 810 of FIG. 8 discussed infra). As such, after a first iteration of estimating the location of the IMD 120, should a user desire to display user interface 190 (or indicia within user interface 190) without performing another assessment of the location of the IMD 120, such information can be retrieved from the device 140 (or the server device 710 or the remote device 810) and can be displayed.

Figure 2:
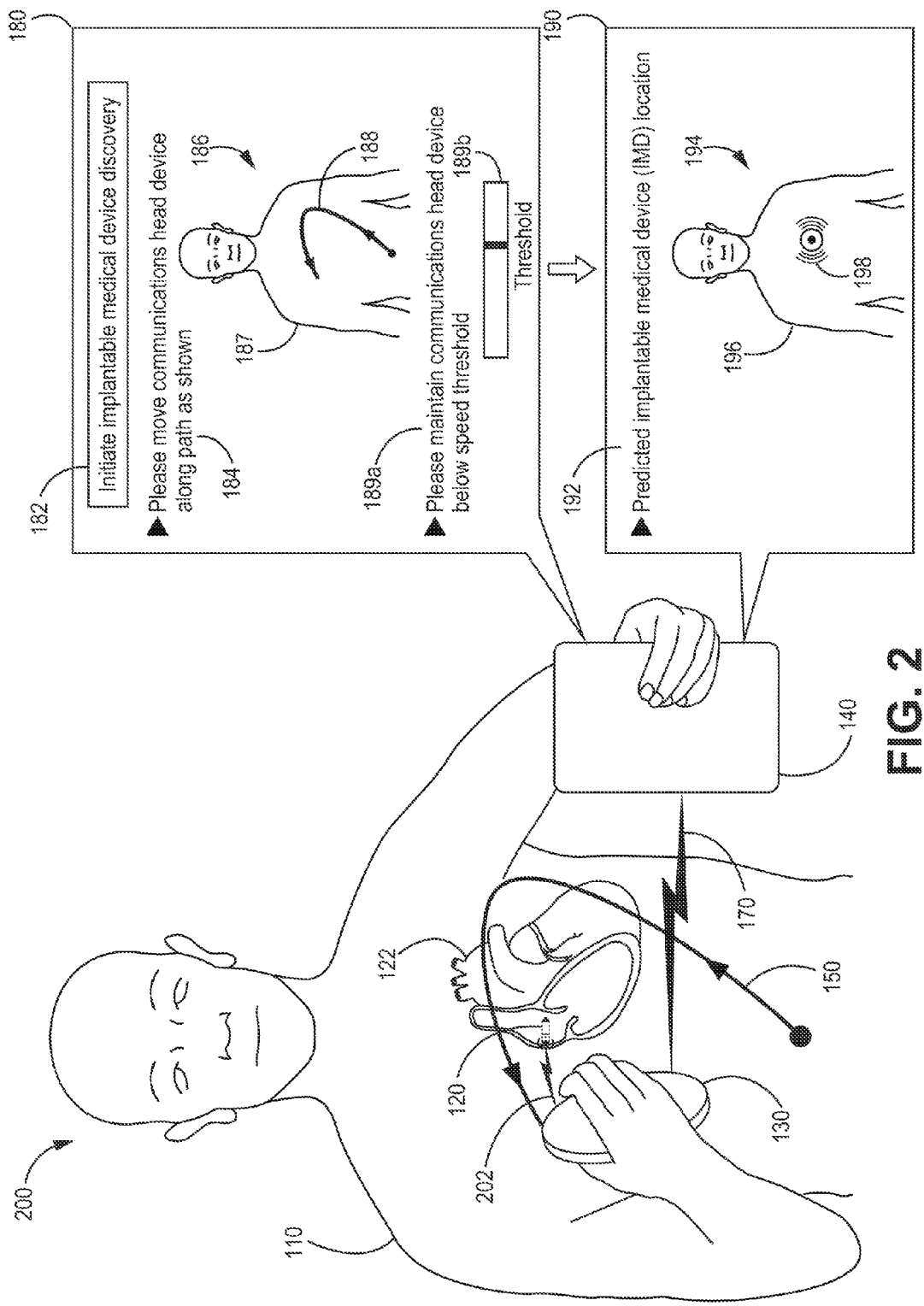

FIG. 2 illustrates a schematic diagram of another example, non-limiting medical device locating system 200 facilitating locating an IMD in accordance with one or more embodiments described herein. Repetitive description of like elements employed in other embodiments described herein is omitted for sake of brevity. While FIG. 1 illustrates an embodiment in which the IMD 120 and the communications head device 130 are inductively coupled, in FIG. 2, the communications head device 130 can be communicatively coupled to the IMD 120 via exchange of electromagnetic (EM) waves. For example, the IMD 120 and the communications head device 130 can be communicatively coupled via an RF signal 202. As in medical device locating system 100, in medical device locating system 200, the communicative coupling between the communications head device 130 and the IMD 120 can be employed to facilitate determination of the location of the IMD 120 within the body 110 as described in various embodiments herein.

Figure 3:
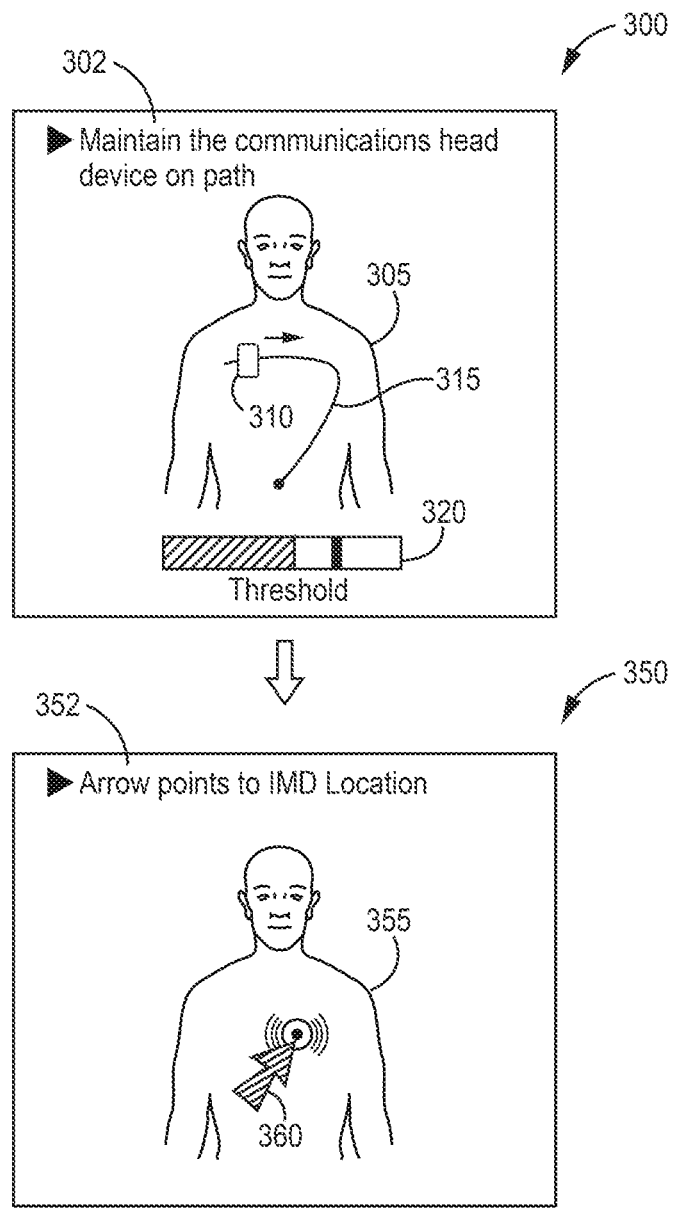
FIG. 3 illustrates schematic diagrams of example, non-limiting user interfaces for determination of location of an IMD within a body in accordance with one or more embodiments described herein.

FIG. 3 illustrates schematic diagrams of example, non-limiting user interfaces for determination of the location of an IMD within a body in accordance with one or more embodiments described herein. Repetitive description of like elements employed in other embodiments described herein is omitted for sake of brevity.

The device 140 can present a user interface 300 as shown in FIG. 3 based on the movement of the communications head device 130. As illustrated, the user interface 300 can include an image 305 of the body 110, an image 310 representative of a current position of the communications head device 130, and the indicia 315 representative of the prescribed path. In some embodiments, as shown, the user interface 300 can include indicia 302 that provides information and/or instructions to the viewer of the user interface 300. As described herein, the indicia 315 can augment the images 305 and 310.

In one example, the images 305 and 310 can be embodied in a single motion picture that can be acquired by a camera of the device 140. Such a motion picture can permit tracking the movement of the communications head device 130 and can be augmented by the indicia 315. It should be appreciated that the device 140 can update the indicia 315 from time to time and/or on a frame-by-frame basis in order to adapt the presentation of the prescribed path to movement of the body 110 and/or the communications head device 130. Augmentation of the images 305 and 310 with the indicia 315 can permit or otherwise facilitate mitigating or avoiding deviations from the prescribed path while traversing the prescribed path, with the ensuing increased likelihood to discovering the IMD 120 without traversal of multiple paths.

In some embodiments, the user interface 350 can be generated as a function of the information received in response to the instructions or other prompts provided via the user interface 300. For example, based on the instructions and/or prompts output via the user interface 300, strength information can be collected that can be utilized to predict the location of the IMD 120 as described herein. Accordingly, in one example, the device 140 can present a user interface 350 including an image 355 and indicia 360 to depict or otherwise convey the predicted location of the IMD 120. In some embodiments, the user interface 350 can include text 352 providing information to the viewer of the user interface 350.

It should be appreciated that, in certain implementations, the device 140 can display or otherwise present the user interface 300 and/or the user interface 350 in lieu of user interfaces 180, 190 described with reference to FIG. 1.

With further reference to FIGS. 1 and 2, the device 140 can receive strength information representative of the communicative coupling between the communications head device 130 and the IMD 120 for multiple locations along the path 150 from the communications head device 130, and can image the movement of the communications head device 130 along the path. Moreover, for each (or, in some embodiments, one or more) of the multiple locations at which strength information is received from the communications head device 130, the device 140 can determine or otherwise identify or estimate a position of the communications head device 130 in coordinates within an image reference frame using such imaging. Such coordinates may be referred to as device coordinates in that the image reference frame can be defined by the device 140 for a specific image acquisition configuration (e.g., field of view, focal distance from the body 110, a combination thereof, or the like) of a camera or other input interface that produces an image of the body 110. Further, the device 140 can match or otherwise associate the identified positions to respective portions of the strength information (e.g., strength data or raw data). More specifically, in an implementation in which the camera acquires video of the movement of the communications head device 130, the device 140 can annotate, time stamp, tag or otherwise modify, e.g., via a timestamp or other metadata, an image frame of a digital representation of the video. For example, the device 140 can annotate or otherwise tag or modify the image frame in response to reception of the strength information. In some embodiments, for such an image frame, the device 140 can generate information indicative of the position of the communications head device 130 in a coordinate reference frame. To that end, the device 140 can analyze the image frame, and identify the communications head device 130 or image features (e.g., color intensity, edge structure, etc.) indicative of the communications head device 130 within the image frame. The communications head device 130 identified within the image frame can be assigned coordinates within a two-dimensional coordinate frame associated with a specific viewpoint of the camera in some embodiments. Such coordinates can be linked or otherwise mapped to the timestamp, tag or annotation to facilitate matching the coordinates (e.g., the location) of the communications head device 130 with strength information.

It should be appreciated that other implementations for determination of the position of the communications head device 130 are contemplated. For instance, in response to or concurrent with receiving strength information, the camera can acquire a still image of the communications head device 130. The image can be time stamped, annotated, tagged or otherwise modified, and a position of the communications head device 130 can be determined, in device coordinates, using the still image. In one example, the strength information can include trigger information (e.g., metadata) that, when received by the device 140, can cause the camera to acquire a still image of the communications head device 130 for image analysis and/or determination of the position of the communications head device 130 based on such analysis. The trigger information can augment or otherwise be combined with the strength information in response to actuation of an input interface that causes the communications head device 130 to measure strength of communicative coupling with the IMD 120.

In another example, estimated velocity of the communications head device 130 can be utilized by the device 140 to estimate a current position of the communications head device 130. Specifically, the device 140 can utilize trigger information to determine a time elapsed since prior reception of strength information and based on such time elapsed and/or the magnitude and direction of the velocity of the communications head device 130, the device 140 can determine or otherwise compute a current position for the communications head device 130. As described herein, the communications head device 130 can transmit velocity information to the device 140. To that end, the communications head device 130 can utilize or otherwise leverage an inertial sensor (e.g., an accelerometer and/or a gyroscope) coupled to or located within the communications head device 130 to facilitate estimation of the location of the communications head device 130.

In yet another example, in lieu of determining a time interval elapsed between successive collection of strength information, the communications head device 130 can generate an output (e.g., emit a sound and/or vibrate) to cause a user of the communications head device 130 to actuate an input interface (e.g., a button) that causes strength information to be acquired and/or reported. The communications head device 130 can generate the output periodically, at defined times, based on the occurrence of particular conditions or the like. Varying the rate at which strength information is received at the device 140 in combination with an estimate of the velocity of the communications head device 130 can facilitate determining positions of the communications head device 130 along a prescribed path.

Thus, regardless of specific implementation, the device 140 can generate a group of triples $\{(Rx, Ry, I)\}$, where $R=(R_x, R_y)$ corresponds to a vector position of the communications head device 130 in the image reference frame, and I corresponds to the magnitude (or other measure of signal strength or signal intensity) for the communicative coupling between the communications head device 130 and the IMD 120 as conveyed by the portion of signal information associated with the position R. Other prescribed paths can be relied upon to generate other triples indicative of the spatial dependence of the strength of the communicative coupling between the communications head device 130 and the IMD 120. By way of example, but not limitation, a prescribed path that spans a greater area than the path 150, for example, can permit or otherwise facilitate generating a group of triples $\{(R'_x, R'_y, I')\}$ with higher density of information than the group of triples generated via the path 150.

Figure 4:
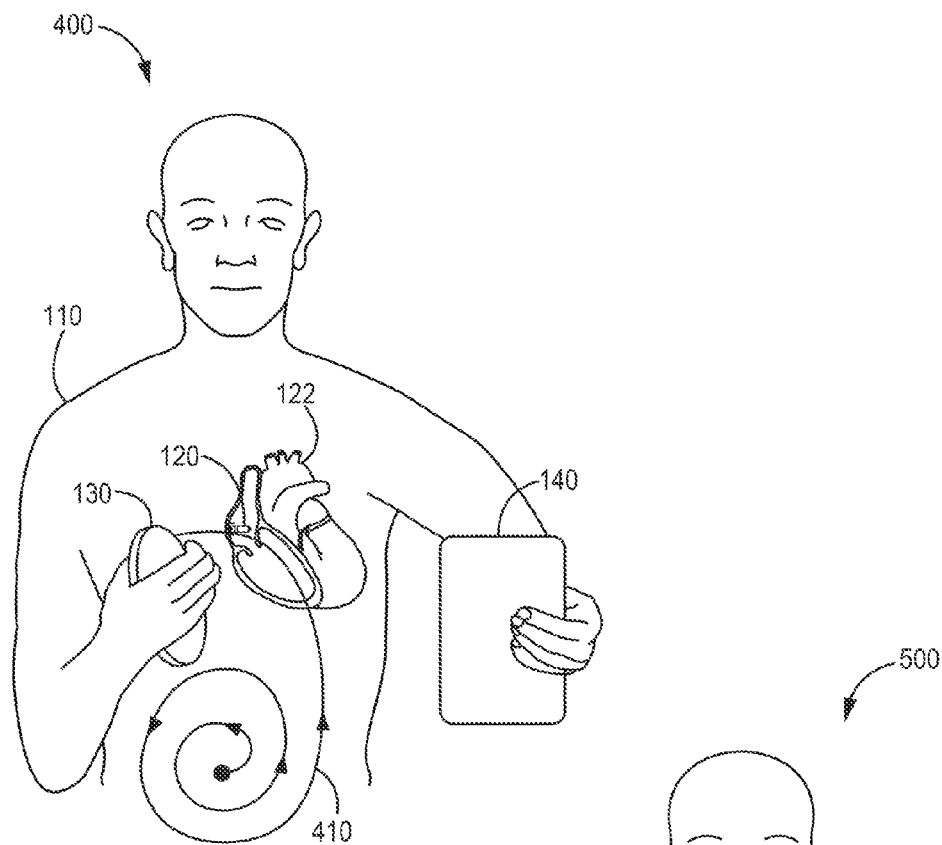
FIGS. 4-5 illustrate schematic diagrams of example, non-limiting embodiments illustrating system operation for locating an IMD in accordance with one or more embodiments described herein.
Figure 5:
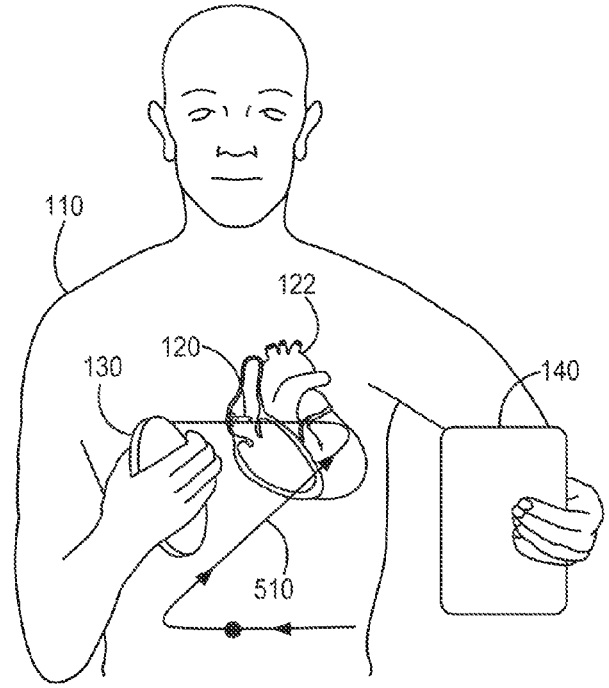

FIGS. 4-5 illustrate schematic diagrams of example, non-limiting embodiments illustrating system operation for locating an IMD in accordance with one or more embodiments described herein. Repetitive description of like elements employed in other embodiments described herein is omitted for sake of brevity. As an example, FIG. 4 illustrates system operation in environment 400 for discovery of the location of an IMD in which a path 410 having substantially spiral geometry is utilized for generation of strength information as described herein. In various embodiments, the starting and ending points can be at any number of positions. In the embodiment shown, the path 410 can have an endpoint at or near the navel (represented with a solid dot) and another endpoint near one of the pectoral muscles in the body 110. As such, the path 410 can cover an area from the upper pelvis to the thorax of the body 110. As another example, FIG. 5 illustrates system operation in environment 500 for discovery of the location of an IMD in which a path 510 having a substantial zigzag geometry is utilized for generation of strength information as described herein. Similar to the path 410, the path 510 can also have an endpoint at or near the navel (represented with a solid dot) and another endpoint near one of the pectoral muscles in the body 110. Accordingly, the path 510 can cover an area from the abdomen to the thorax of the body 110. In other instances, the paths 410 and 510 may be more specifically generated for a particular type of IMD 120. For example, path 410 may follow the spiral geometry in a smaller space proximate the pectoral region (e.g., left pectoral region) instead of the entire thorax for a patient have a cardiac loop recorder, leadless pacemaker, or pressure sensor in the vasculature. Likewise, path 510 may be more concentrated in the pectoral region (e.g., left pectoral region) for a cardiac IMD 120.

A group of triples $\{(Rx, Ry, I)\}$ associated with a prescribed path (e.g., path 150, 410, or 510) can represent a strength map corresponding to the strength of the communicative coupling as a function of position of the communications head device 130 within an area containing or otherwise in the vicinity of the prescribed path. Here, $R=(R_x, R_y)$ can correspond to a vector position of the communications head device 130 in a coordinate frame associated with the device 140, and I can correspond to the magnitude (or other measure of signal strength or signal intensity) for the communicative coupling between the communications head device 130 and the IMD 120.

Figure 6:
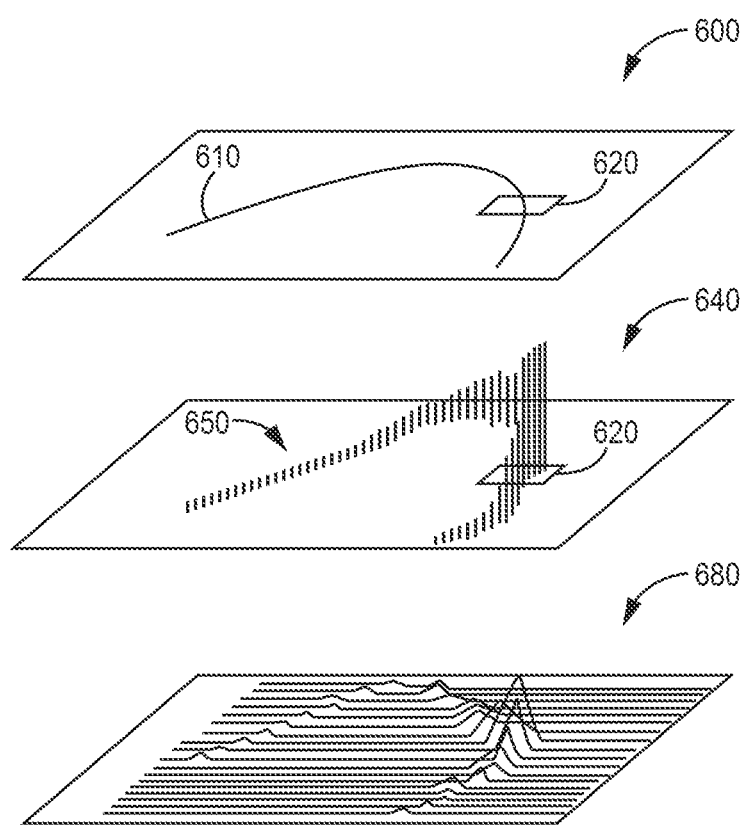
FIG. 6 illustrates a series of formation of schematic diagrams for generating an example, non-limiting strength map in accordance with one or more embodiments described herein.

FIG. 6 illustrates a series of formation of schematic diagrams for generating an example, non-limiting strength map in accordance with one or more embodiments described herein. Repetitive description of like elements employed in other embodiments described herein is omitted for sake of brevity. As illustrated, diagram 600 represents a projection 610 of a prescribed path (e.g., path 150) onto a plane. For reference, the diagram 600 can also illustrate a marking 620 representative of the position of the IMD 120. Also shown in FIG. 6 is a diagram 640 that includes a group of multiple markings 650 (e.g., straight segments). One or more of the markings can be representative of the magnitude of the strength of the communicative coupling between the communications head device 130 and the IMD 120 at different locations of the communications head device 130 along the projection 610. As such, the group of multiple markings 650 shown in diagram 640 can represent the information that can be gleaned from a group of triples {(Rx, Ry, I)}. Intensities at positions near the region in which the IMD 120 is located are greater than intensities at positions distant from such a region since the communicative couplings between the communications head device 130 and the IMD 120 will be greater when the communications head device 130 is closer to the IMD 120.

As described herein, in certain implementations, the device 140 can interpolate and/or extrapolate values of the intensities using the group of triples {(Rx, Ry, I)} and/or can generate a denser representation of strength map characterized by the group of multiple markings 650. Diagram 680 in FIG. 6 depicts such a representation, which can permit a more accurate determination of an estimate of the location of the IMD 120.

With further reference to FIG. 1, the device 140 can utilize or otherwise leverage a strength map as described herein in order to determine or otherwise estimate a location of the IMD 120 within an area of the body 110 containing the path 150. As such, in one or more embodiments, the device 140 can identify a triple ($R_x$, $R_y$, I) in the strength map having the largest magnitude (or intensity or signal strength) and assign the position in such a triple to the location of the IMD 120. In other implementations, the device 140 can predict a position at which the magnitude (or intensity or signal strength) of the communicative coupling would be maximal. The device 140 can store in memory (e.g., one or more computer readable storage devices) the strength map and/or the estimate of the location of the IMD 120. The device 140 can utilize the stored information at a later time (in lieu of collecting additional strength information and/or performing another estimation of the location of the IMD 120) when communication between the communications head device 130 and the IMD 120 is desired.

To that end, in one example, the device 140 can interpolate values of strength in a grid of positions that can be denser than the actual positions of the triples {($R_x$, $R_y$, I)} and/or can span a greater portion of the area of the body 110. The device 140 can then determine a maximum of the strength using the interpolated values of strength and/or the measured values of strength. The device 140 can assign the position of such a maximum to the location of the IMD 120. It should be appreciated that regardless of embodiment, rather than determining the largest or maximal strength, the device 140 can utilize a threshold and can assign the location of the IMD 120 to a position that yields a strength magnitude greater than or equal to the threshold. The threshold can be configurable (and therefore can be changed from time to time) and/or can be determined based on the values of strength magnitude within the strength map (e.g., the threshold can be $0.9 I_{max}$, where $I_{max}$ is the largest magnitude in the strength map). It should be readily appreciated that the greater the coverage of the path 150 over an area of the body 110, the more accurate the determination of the estimate of the location of the IMD 120 can be. For instance, as described herein, paths 410 and 510 can permit or otherwise facilitate generating richer strengths maps than the strength map associated with the path 150.

A determination of the location of the IMD 120 within the body 110 can cause the device 140 to generate imaging information (digital or otherwise) representative of the estimated location and at least a portion of the body 110. Therefore, in certain implementations, the device 140 can generate, via a camera, for example, an image of the body 110. The image of the body 110 can be embodied in or can include a motion picture or a still picture. Information representative of the image can constitute such imaging information. In addition, the device 140 can generate indicia information to convey the position of the IMD 120 within a reference frame associated with the image of the body 110. The indicia information can augment the information representative of the image of the body 110 and/or can be included in the imaging information.

In addition, the device 140 can present indicia representative of at least a portion of the imaging information. For instance, as described herein, the device 140 can present a user interface 190 including indicia 192 that introduces a predicted location of the IMD 120. The user interface 190 can also include indicia 194 representative of a combination of an image 196 of a portion of the body 110 and/or indicia 198 that conveys the position of the IMD 120 relative to the imaged portion of the body 110. In one embodiment, the indicia 194 can represent a motion picture of the body 110 and/or placement of the indicia 198 can be updated according to the movement of the body 110. Other indicia besides the indicia 198 can be presented. As illustrated in FIG. 3 and described herein, the device 140 can present a user interface 350 including an image 355 and indicia 360 to convey graphically the predicted location of the IMD 120.

It should be appreciated that while various embodiments are described in connection with a single IMD, the embodiments described herein are not limited in this respect and the device 140 and/or other computing devices described herein also can generate respective strength maps for any number of IMDs within a body. Each of the generated strength maps can be utilized to predict or otherwise determine an estimate of the position of a corresponding IMD in accordance with aspects described herein.

In some embodiments, various different types of information can be saved and/or presented to or transmitted to the device 140. In certain embodiments, at least a portion of the functionality associated with determining an estimate of the location of the IMD 120 can be accessed as a service in a client-server configuration. The service can provide, for example, storage of strength information, strength maps, estimates of locations of an IMD, imaging information, user interface information, a combination of the foregoing, or the like. The service also can provide, for example, computation functionality to predict or otherwise determine a position of an IMD within a body based on strength information as described herein. In such embodiments, a server device (not shown) external to the device 140 can perform at least some of the operations associated with determining the estimate of the location of the IMD 120. The device 140 can operate as a client of the server device, exchanging information with the device 140 and/or presenting (e.g., displaying) at least a portion of the received information.

In certain implementations, the device 140 can also process (e.g., format and/or render) at least a portion of the received information prior to displaying the received information or a representation of the received information. More specifically, in one example, FIGS. 7-8 illustrate schematic diagrams of example, non-limiting medical device locating systems 700, 800 facilitating locating an IMD in accordance with one or more embodiments described herein. Repetitive description of like elements employed in other embodiments described herein is omitted for sake of brevity.

Turning first to FIG. 7, illustrated is an example, non-limiting medical device locating system 700 facilitating locating the IMD 120 as a service and/or utilizing information provided via server device 710 to facilitate locating of the IMD 120. As illustrated, the device 140 can be functionally coupled (e.g., communicatively, electrically, and/or electromechanically coupled) to a server device 710 via one or more of links 715. The links 715 can include an uplink and/or a downlink in various embodiments, one or more of links 715 can be embodied in or including a wireless link or a wireline link. More specifically, yet not exclusively, the links 715 can include one or more of a satellite wireless link, a cellular wireless link, a confined-access wireless link (such as a Wi-Fi or a femtocell wireless link), an access point device or other types of base stations, a gateway device, a router device, an aggregator device, optical fiber lines, coaxial lines, a combination of the foregoing, or the like.

Regardless of the type of coupling between the device 140 and the server device 710, the server device 710 can receive strength information and positioning information from the device 140. As described herein, the strength information can be representative of a communicative coupling between the communications head device 130 and the IMD 120 as a function of position along the path 150. The positioning information can be representative of multiple locations of the communications head device 130 along the path 150. The server device 710 can match the strength information to the positioning information. For instance, for each (or, in some embodiments, one or more) of the multiple locations conveyed by the positioning information, the server device 710 can associate a portion of the strength information to a location along the path 150. Based on such association, the server device 710 can determine a strength map in accordance with aspects of this disclosure. In addition, the server device 710 can determine an estimate of the location of the IMD 120 within the body 110 using the strength map.

The server device 710 can send (e.g., transmit or otherwise communicate) an estimate of the location of the IMD 120 to the device 140. In response, the device 140 can present the user interface 190 as described herein.

In some embodiments, the server device 710 can store and/or serve patient information. For example, the patient information stored at the server device 710 can be associated with body size of a patient and/or a medical condition of the patient. The device 140 can receive at least a portion of patient information stored in the server device 710 and/or accessible from the server device 710. Based on such information, the device 140 can determine that the location information for an IMD 120 should be updated. For example, if the size of the body of a patient or a condition occurs over time (e.g., pregnancy or osteoporosis), a determination can be made to re-determine new location information for the IMD as the previously-determined location information may not be accurate and/or there is a defined likelihood that placement of the communications head device 130 at the previously-estimated location for the IMD 120 will not yield a communicative coupling having a strength that satisfies a defined criterion. In the alternative, the device 140 can determine, based on the received patient information, that the location information for the IMD 120 determined using a current strength map as described herein is valid and should not be updated.

In some embodiments, generating the strength map can be performed at initial configuration or setup of the device 140 (or communications head device 130) and/or at regular intervals after a defined number of uses of the communications head device 130. However, in various embodiments, upon start-up or login into the device 140, in embodiments in which one or more triggers do not occur or conditions are not applicable, device 140 can load strength map information previously saved and immediately direct the user to the location of the IMD 120 (e.g., output the indicia representative of the location of the IMD 120 and/or direct the user of the communications head device 130 to the location of the IMD 120 via audio or haptic signals) without need for a new process for signal strength collection to be performed. In this embodiment, if one or more triggers do not occur or conditions are not applicable (e.g., a defined amount of time has not elapsed since last collection of signal strength information, patient medical condition has not changed, patient body size has not changed more than a defined amount), the device 140 would proceed with operations based on a determination that the previously determined location of the IMD 120 continues to be a valid location. In some embodiments, if a signal strength between the IMD 120 and the communications head device 130 is weaker than expected upon placement of the communications head device 130 at the location of the IMD 120 indicated by the device 140, or if communication between the IMD 120 and the communications head device 130 is unsuccessful, a new process of collecting signal strength information to generate information indicative of an updated strength map and/or an updated location of the IMD 120 can commence. In some embodiments, when the communications head device 130 is placed on the body 110 of the patient, data in the map can be updated for the signal triplets measured.

Turning now to FIG. 8, another example, non-limiting medical device locating system 800 is shown. Communicative coupling (inductive coupling and/or RF coupling) between the IMD 120 and the communications device is generically represented with a bi-directional link 805. In this embodiment, a remote device 810 can operate as a peripheral device to the device 140 and can provide at least some of the functionality associated with imaging of the body 110 and/or the communications head device 130. For instance, the remote device 810 can be embodied in or can include a camera that can produce imaging information representative of the body 110 or a portion thereof, and/or a display device that can display information. The remote device 810 and the device 140 can exchange information (e.g., strength information, imaging information, or the like) via links 815 (wireless or wireline links).

Based at least on information received from the remote device 810, the device 140 can provide processing functionality associated with determining a strength map and/or an estimating the location of the IMD 120 using the strength map in accordance with aspects described herein. Upon or after such an estimate has been determined, the device 140 can send imaging information indicative of the user interface 190 and/or indicia displayed via the user interface 190 for presentation by the remote device 810.

Figure 9:
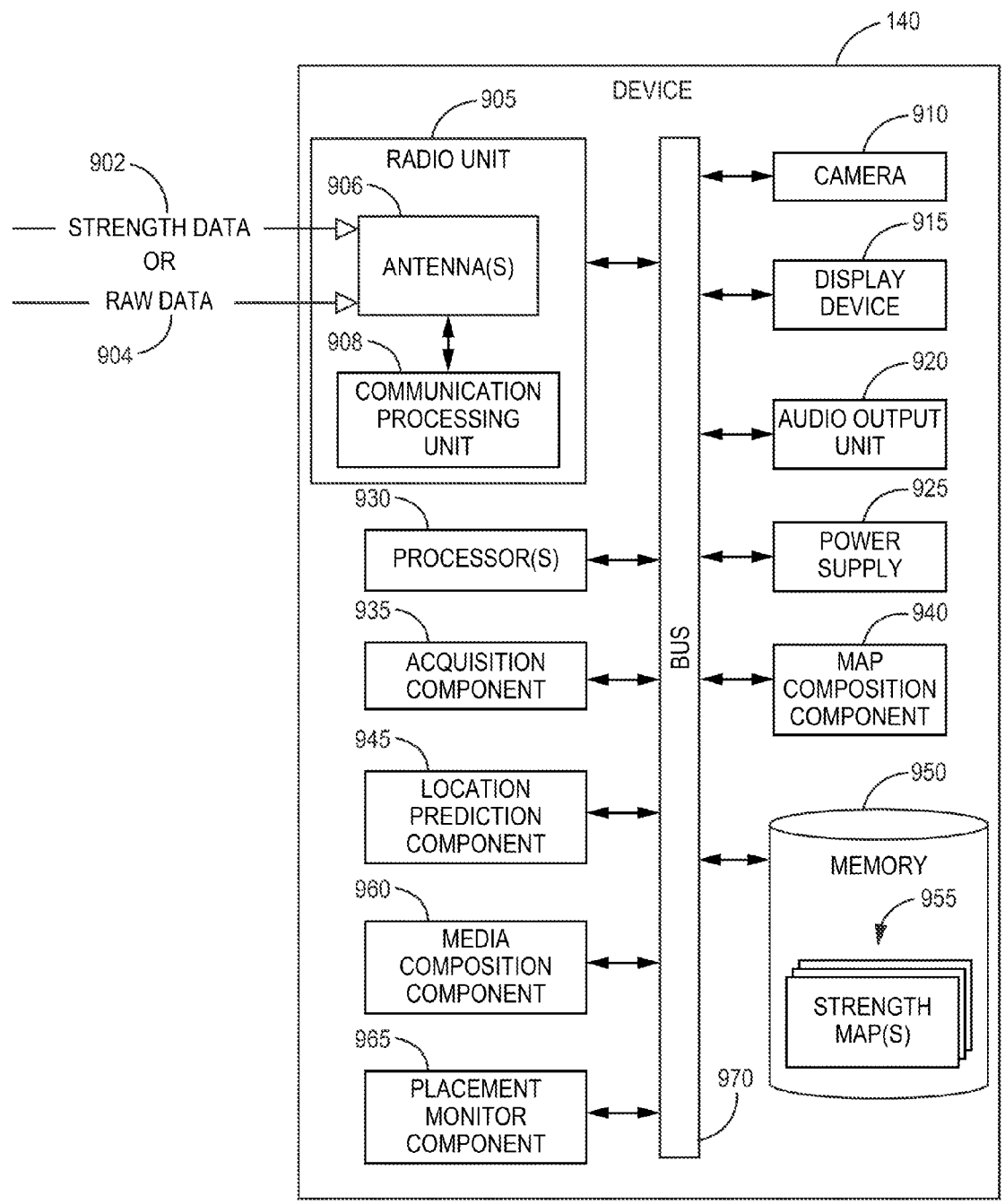
FIGS. 9-10 illustrate block diagrams of example, non-limiting devices facilitating locating an IMD in accordance with one or more embodiments described herein.
Figure 10:
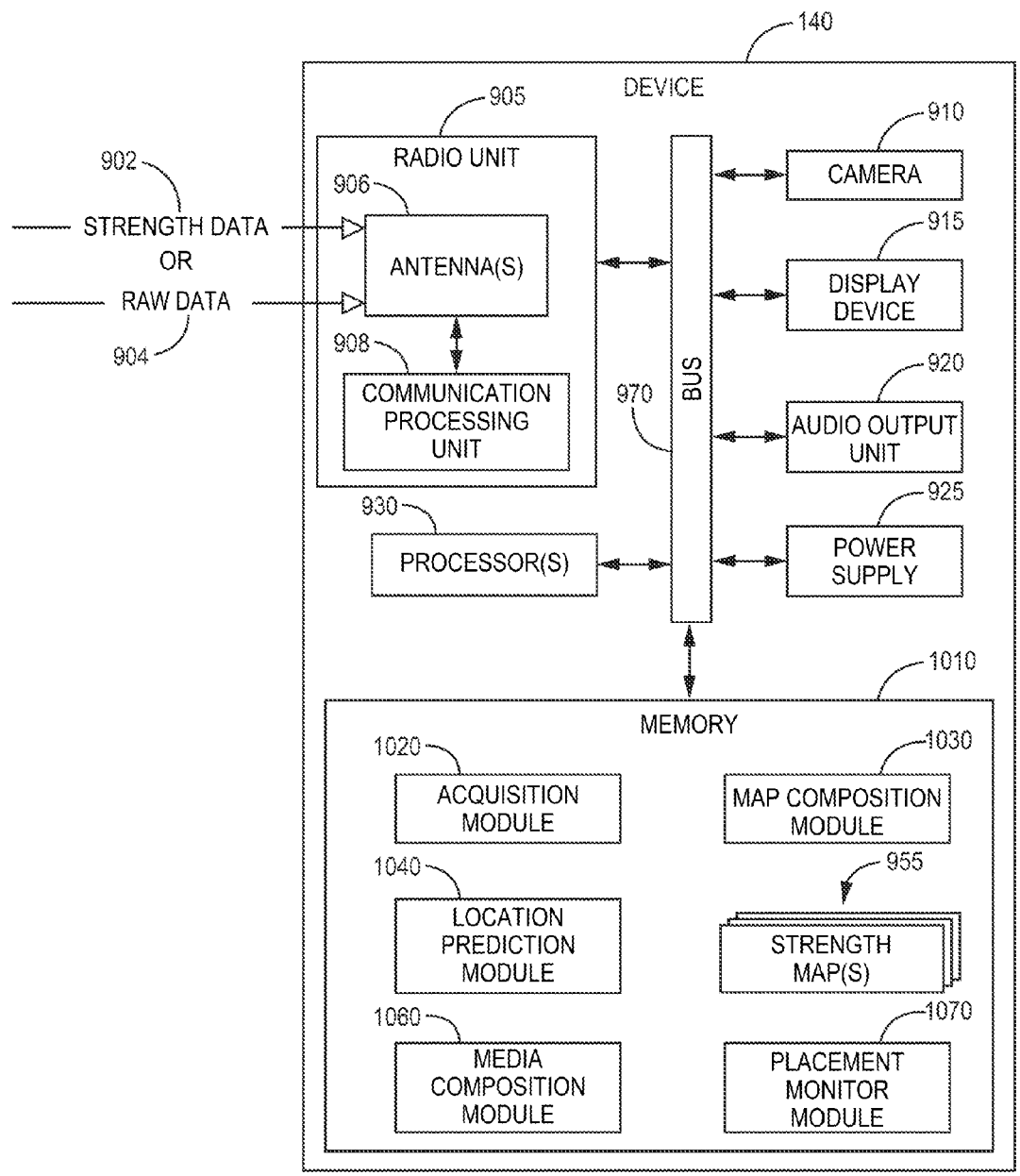

FIGS. 9-10 illustrate block diagrams of example, non-limiting devices facilitating locating an IMD in accordance with one or more embodiments described herein. Repetitive description of like elements employed in other embodiments described herein is omitted for sake of brevity.

As shown in FIG. 9, the device 140 includes a radio unit 905 that can receive strength information wirelessly from a communications head device, such as communications head device 130. The strength information can be representative or otherwise indicative of the strength of a communicative coupling between the communications head device and an IMD, such as IMD 120. As such, in certain embodiments, the strength information can include a device ID indicative of the IMD 120 or another IMD located in the body of the patient. For instance, the strength information can be augmented or otherwise tagged with metadata indicative of the device ID. In certain implementations, as described herein, the strength information can include strength data 902 indicative or otherwise representative of the magnitude (or intensity) of such communicative coupling. In other implementations, as described herein, the strength information can include raw data 904 that can be processed by the device 140 in order to determine the magnitude of the communicative coupling between the communications head device and the IMD.

The radio unit 905 can include one or more antenna(s) 906 that can receive the strength data 902 or the raw data 904. Each of these data can be modulated and/or encoded according to a specific radio technology protocol, which can be embodied, in some embodiments, in a point-to-point short-range communication protocol, such as BLUETOOTH® low energy (LE), ZigBee®, or other proprietary or non-proprietary communication protocols. As such, the radio unit 905 can include a communication processing unit 908 that can demodulate, decode, and/or otherwise process the received strength data 902 or raw data 904.

In the illustrated embodiment, the device 140 also includes a camera 910 that can generate imaging information (e.g., analog data and/or digital data) representative or otherwise indicative of an image of a body and the communications head device that sends the strength data 902 or the raw data 904. In one example, the camera 910 can include an optics module including lens(es), collimator(s), support member(s), and/or other types of elements that permit collecting light from the body in which the IMD is implanted and/or the communications head device. In addition, the camera 910 can include an imaging module that can receive at least a portion of the collected light and can generate the imaging information. The device 140 also includes one or more processors 930, where at least one of the processor(s) 930 can control the operation of the camera 910, such as control of an auto-focus (AF) module that can be included in the optics module.

In addition, the device 140 includes an acquisition component 935 that can receive at least a portion of the imaging information and can operate on the received imaging information in order to extract features or aspects of the imaging information. As described herein, in one example, the acquisition component 935 can extract a position, in device coordinates, of the communications head device (e.g., communications head device 130) imaged by the camera 910. As such, as the camera 910 images the movement of the communications head device, the acquisition component 935 can extract or otherwise generate position information indicative of multiple locations, in device coordinates, of the communication head device along a path. Stated in different terms, the acquisition component 935 can track the position of the communications head device using imaging information generated by the camera 910. The acquisition component 935 can tag or otherwise mark (with metadata, for example) a portion of the position information corresponding to a particular location within the set of multiple locations. As described herein, the communications head device 130 can traverse a prescribed path (e.g., path 150) and, therefore, the acquisition component 935 can track the movement of the communications head device 130 along the path. To that end, in one embodiment, the acquisition component 935 can generate position information indicative or otherwise representative of the prescribed path. In one implementation, the position information can be indicative or otherwise representative of the prescribed path in its entirety.

In another implementation, the position information can dynamically define the prescribed path in response to analysis of strength information or other type of information. By way of example, but not limitation, the acquisition component 935 can analyze strength information (e.g., compare current strength information with historical strength information) and determine or otherwise predict a next one or more positions for placement of the communications head device 130 in order to improve strength of communicative coupling between the communications head device 130 and the IMD 120. In some embodiments, the information so determined can be combined with extant or otherwise current position information in order to update or further define a current prescribed path. Accordingly, in some embodiments, the path for collection of strength information can be dynamically prescribed as the communications head device 130 is moved about the body.

The device 140 can also include a media composition component 960 that can generate imaging information indicative or otherwise representative of the prescribed path. The imaging information can be generated statically or dynamically depending on the manner in which the position information related to the prescribed path is generated.

The acquisition component 935 can also receive, from the radio unit 905, for example, at least a portion of the strength information. In a scenario in which the strength information is embodied in or includes strength data 902, the acquisition component 935 need not operate on the strength information. In a scenario in which the strength information is embodied in or includes raw data 904, the acquisition component 935 can generate metrics representative of strength of communicative coupling using at least a portion of the raw data 904. Such metrics can correspond to strength data associated with the strength of the communicative coupling between a communications head device and an IMD. The acquisition component 935 can tag or otherwise mark (with metadata, for example) portions of the strength data—either received strength data 902 or strength data generated by the acquisition component 935.

The acquisition component 935 can send position information (tagged or non-tagged) associated with a communications head device to a map composition component 940. In addition, the acquisition component 935 can send strength data (tagged or non-tagged) associated with the communications head device and an IMD to the map composition component 940. The map composition component 940 can receive the position information and the strength data, and can associate a portion of the strength data to a portion of the position information. The portion of the strength data can correspond to a metric indicative of the strength of the communicative coupling between the communications head device and the IMD at a specific position of the communications head device relative to the IMD. The portion of the position information can be indicative of such a specific position. Therefore, the map composition component 940 can match portions of the strength data to respective portions of the position information corresponding to multiple locations along a path (e.g., path 150, path 410, path 510, or the like) in which the communications head device is moved relative to the IMD. The matching of the strength data to the position information can yield a strength map. The map composition component 940 can retain the strength map within a memory 950, as one or more strength maps 955. The memory 950 can be embodied in or can include one or more computer-readable storage devices.

It should be appreciated that, in scenarios in which multiple IMDs (e.g., an atrial leadless pacemaker and a ventricular leadless pacemaker) are implanted in a single body, the device 140 can generate a strength map for each of the multiple IMDs. To that end, in one example, the acquisition component 935 can distinguish strength information (e.g., strength data 902 or raw data 904) for each of the IMDs, via respective device IDs, for example, and the map composition component 940 can generate a strength map for each IMD. Each of the strength maps so generated can be stored in memory 950, within the strength map(s) 955. In some embodiments, the acquisition component 935 can also store information indicative of an overlap region at which two or more strength maps overlap. In different embodiments, there can be any number of overlap regions based on the number of IMDs within the body, the shape of the regions indicated by the strength maps, the proximity of the IMDs to one another, the relative signal strengths of the IMDs and the like.

The device 140, as illustrated in the example embodiment, can also include a location prediction component 945 that can receive a strength map from the map composition component 940 and/or can access the strength map from the memory 950. The location prediction component 945 can determine an estimate of the location of an IMD using the strength map as described herein. The location prediction component 945 can configure such an estimate as the location of the IMD within the body imaged by the camera 910 and/or scanned via a communications head device communicatively coupled to the IMD.

An estimate of the location of an IMD represents the implant location. In response to a determination of the implant location, the device 140 can present a user interface that conveys indicia representative of the implant location and an image of at least a portion of a body in which the IMD is implanted. For instance, the user interface can be embodied in or can include the user interface 190 described in connection with FIG. 1, and a display device 915 can present the user interface. It should be readily appreciated that the indicia can augment such an image (e.g., motion picture or a still picture of the body) thereby providing a rich augmented-reality interface that readily identifies the location of the IMD relative to the body.

To that end, with further reference to FIG. 9, in one embodiment, the device 140 can leverage or otherwise utilize the media composition component 960 to generate imaging information indicative or otherwise representative of the implant location and at least the portion the body. As such, the imaging information can include marking information indicative of the indicia representative of the implant location and other body information indicative of the image of at least the portion of the body. The indicia can be embodied in or can include an icon, a thumbnail, or another type of graphical media. At least a portion of the body information can be received from the camera 910. In a scenario in which the image of at least the portion of the body is a motion picture (e.g., a video of the body), the body information can include frame information indicative of multiple image frames. In such scenario, in one example, the media composition component 960 can generate marking information representative of respective indicia for each (or, in some embodiments, one or more) of the multiple frames. The respective indicia can represent the implant location in each (or, in some embodiments, one or more) of the multiple frames. Accordingly, the user interface presented by the device 140 can convey the implant location relative to the body regardless of movement of the body.

After an initial determination of an implant location, the device 140 can query or otherwise access a stored strength map and can display indicia representative of the implant location relative to a body in which the IMD is implanted. In addition, in a scenario in which exchange of information between the communications head device and the IMD is desired, the device 140 can determine whether the placement of a communications head device relative to a body can be adequate for communication with an IMD implanted in the body. For example, the adequacy of the placement can be determined based on a coupling criterion that can establish a threshold for the magnitude of the communicative coupling between the communications head device and the IMD.

With further reference to FIG. 9, in the example embodiment shown, the device 140 includes a placement monitor component 965 that can permit such a determination. In one implementation, the placement monitor component 965 can instruct or otherwise cause the media composition component 960 to generate imaging information indicative or otherwise representative of a location of an IMD within an area of a body. Such a location can be referred to as an implant location, and can be determined from a strength map representative of strength of a communicative coupling between a communications head device and the IMD as a function of position within such an area. In one example, the media composition component 960 can access location information indicative of the implant location from the memory 950 or other computer-readable storage device coupled to the device 140. In addition, the media composition component 960 can instruct or otherwise cause the display device 915 to present at least a portion of such imaging information. Further, the media composition component 960 can generate other imaging information representative of a prompt place the communications head device (e.g., communications head device 130) in proximity to the implant location. The media composition component 960 can direct or otherwise cause the display device 915 to present at least a portion of the second imaging information.

The prompt to place the communications head device in proximity to the location of the IMD can be selectable or otherwise actionable. In response to selection of the prompt, the placement monitor component 965 can cause the device 140 to send, to the communications head device, an instruction to provide strength information (e.g., strength data and/or related unprocessed, raw data) representative of strength of a signal received from the IMD at a current location of the communications head device. The instruction can be generated by the placement monitor component 965 and can be sent via the radio unit 905. Accordingly, the placement monitor component 965 can receive strength data from the communications head device, via the radio unit 905 and the acquisition component 935, for example. In the alternative, the acquisition component 935 can generate the strength data using raw data received from the communications head device via the radio unit 905. Regardless of the source of the strength data, the placement monitor component 965 can determine whether the strength conveyed by the strength data is greater than or equal to a specific strength threshold. Such a threshold can be configurable and represents a suitable magnitude of a communicative coupling between the communications head device and the IMD. Thus, placement of the communications head device at a location that yields a strength magnitude greater than or equal to the specific strength threshold (which can embody a coupling or placement criterion) can be deemed to be adequate for communication between the communications head device and the IMD.

Further, the suitability of a communicative coupling can vary depending on the orientation of the IMD within the body of the patient. In one embodiment, maximum strength intensity can be determined to be at a first location if the IMD is oriented in a first direction within the body while the maximum strength intensity can be determined to be at a second location on the body if the IMD is oriented in a second direction within the body. Accordingly, in certain embodiments, the media composition component 960 can generate orientation information to be presented by the device 140 in a user interface (e.g., user interface 180 or user interface 190) that prompts a patient or end-user to place the communications head device 130 in a specific orientation. It should be appreciated that, in certain implementations, orientation information can be particularly pertinent in view that construction of a communications head device can be orientation dependent.

In response to an adequate or otherwise satisfactory placement of a communications head device relative to an IMD, the device 140 can provide an indication of such placement. The indication can be provided via an output interface within the device 140, and can include an audio output signal, a video output signal, and/or a haptic signal (such as a vibration). The audio output signal and/or the video output signal can represent media that conveys a sound, a screen or graphical interface update, an icon flash, a combination thereof, or the like.

In one implementation, with further reference to FIG. 9, the placement monitor component 965 can cause the display device 915 to output the video output signal and also can cause an audio output unit 920 to output the audio output signal. The audio output unit 920 can include a sound speaker and amplifiers, filters, and/or other circuitry for generation or otherwise processing of audio signals. The media composition component 960 can generate at least a portion of the media represented by the audio input signal and/or the video output signal. In addition or in other implementations, the placement monitor component 965 can cause a haptic device (not depicted in FIG. 9) to provide the haptic signal. Further, or in other implementations, the placement monitor component 965 can cause the device 140 to send an instruction to the communications head device to cause the communications head device to provide a second indication of adequate placement of the communications head device. The second indication also can include an audio output signal, a video output signal, and/or a haptic signal.

As described herein, in some embodiments, location estimates and strength information (e.g., strength data 902 or raw data 904) can be gathered each time a communications head device is utilized for communication with an IMD. Therefore, an extant strength map generated by the device 140 or otherwise available (e.g., retained in a remote device) can be updated with additional strength information. Such an update can permit accounting for changes to communication strength characteristics between the communications head device and the IMD that can originate from changes, over time, in the IMD (e.g., diminished battery charge) or in the body that hosts the IMD (e.g., patient size changes, device position changes, and so forth). Updates to the strength information and an estimate of the location of the IMD can be implemented periodically or at scheduled times or when communication in the previously determined location is not satisfactory in order to determine current estimate of the location of the IMD.

As such, with further reference to FIG. 9, the map composition component 940 can generate information indicative of an updated strength map based on updated strength information. As described herein, the updated strength information can be accessed by the device 140 in response to a change in a size of the body or a time interval that has elapsed since previous generation of a strength map.

In addition to or in certain implementations, the device 140 can determine or otherwise predict that the location of an IMD within a body has changed. To that end, with further reference to FIG. 9, the acquisition component 935 can access information associated with a current state of health of the body, and based on at least a portion of such information, the location prediction component 945 can determine that the IMD is located at a new implant location. In one example, the location prediction component 945 can determine the new implant location autonomously, using models for drift or other positional changes of the implantable device based on health conditions or other characteristics of the body. Such models can be generated, for example, based on aggregated patient information (anonymized or otherwise) associated with positioning of IMD in patients having a specific health condition or specific body characteristics. The device 140 can access such models from a remote device (e.g., server device 710). In response to a predicted change in the location of the implanted medical device, the map composition component 940 can generate information indicative of an updated map, and can retain such a map in the memory 950.

Two or more of the functional elements included in the device 140 in the example embodiment shown in FIG. 9 can exchange information (e.g., data, metadata, and/or signaling) via a bus 970. The bus 970 can be embodied in or can include a system bus, a memory bus, a control bus, a combination thereof, or any other type of bus architecture for the exchange of information. The bus 970 can permit wireless communication (e.g., optically switched communication), wireline communication, or a combination of both. In addition, the device 140 can include a power supply 925 that can energize one or more functional elements that operate within the device 140. In one example, the power supply 925 can include one or more transformers to achieve power level(s) to operate the device 140 and the functional elements and related circuitry therein. In addition or in another example, the power supply 925 can be embodied in or can include a rechargeable or non-rechargeable battery. As such, the power supply 925 can attach to a conventional power grid to recharge, or ensure that the device 140 is operational. To that end, the power supply 925 can include input/output (I/O) interface(s) (not shown), or connector(s) (not shown), to functionally attach to the conventional power grid. In another example, the power supply 925 also can include an energy conversion component (not shown) such as a solar panel, a thermoelectric device or material, and/or another type of energy storage material (which can be external or internal to the device 140) in order to provide additional or alternative power resources or autonomy to the device 140.

Each (or, in some embodiments, one or more) of the components illustrated in the example embodiment 900 of the device 140 can include circuitry to process information and provide the functionality described herein in connection with discovery of a location of an IMD in accordance with one or more embodiments described herein. One or more components in the example embodiment can be embodied in an integrated circuit or chipset having processing elements and/or storage elements, such as an application specific integrated circuit (ASIC), a programmable field gate array (PFGA), or the like. As such, the example embodiment may be referred to as a firmware embodiment. It should be appreciated that other embodiments are contemplated, as shown in FIG. 10.

FIG. 10 illustrates a block diagram of an example, non-limiting device facilitating locating an IMD in accordance with one or more embodiments described herein. Repetitive description of like elements employed in other embodiments described herein is omitted for sake of brevity. As illustrated, in the embodiment shown in FIG. 10, the device 140 can include a memory 1010 that can retain a group of modules, each configured to perform at least some of the functionality described herein. Specifically, a module can perform such functionality in response to being executed by at least one of the processor(s) 930. Accordingly, the acquisition module 1020 can be configured to provide the functionality of the acquisition component 935 as described herein. At least one of the processor(s) 930 can execute the acquisition module 1020 to provide or otherwise facilitate the functionality of the acquisition component 935 as described herein.

In addition, the map composition module 1030 can be configured to provide the functionality of the map composition component 940 as described herein. At least one of the processor(s) 930 can execute the map composition module 1030 to provide or otherwise facilitate the functionality of the map composition component 940 as described herein. Further, the location prediction module 1040 can be configured to provide the functionality of the location prediction component 945 as described herein. At least one of the processor(s) 930 can execute the location prediction module 1040 to provide or otherwise facilitate the functionality of the location prediction component 945 as described herein.

Furthermore, the media composition module 1060 can be configured to provide the functionality of the media composition component 960 as described herein. At least one of the processor(s) 930 can execute the media composition module 1060 to provide or otherwise facilitate the functionality of the media composition component 960 as described herein. In addition, the placement monitor module 1070 can be configured to provide the functionality of the placement monitor component 965 as described herein. At least one of the processor(s) 930 can execute the placement monitor module 1060 to provide or otherwise facilitate the functionality of the placement monitor component 965 as described herein.

The memory 1010 can be embodied in or can include one or more computer-readable storage devices. In one implementation, each of the modules retained in the memory 1010 can be embodied in computer-readable storage device including computer-executable instructions. In another implementation, a module retained in the memory 1010 can be distributed across two or more of the computer-readable storage devices that can constitute the memory 1010. A module retained in the memory 1010 can include computer-executable instructions or other type of computer-accessible code (e.g., computer-readable programming code and/or computer-executable programming code). At least a portion of the computer-executable instructions or at least a portion of the other type of computer-accessible code can be configured to be executed by at least one of the processor(s) 930. Therefore, the module itself can be configured to be executed by the at least one processor.

Each (or, in some embodiments, one or more) of the modules retained in the memory 1010 can be configured to provide functionality associated with discovery of the location of an IMD in accordance with one or more embodiments. Specifically, the computer-executable instructions or other type of computer-accessible code that can constitute a module can be configured to cause the device 140 to provide certain functionality of discovery of the location of an IMD in response to execution of the module by at least one of the processor(s) 930.

Figure 11:
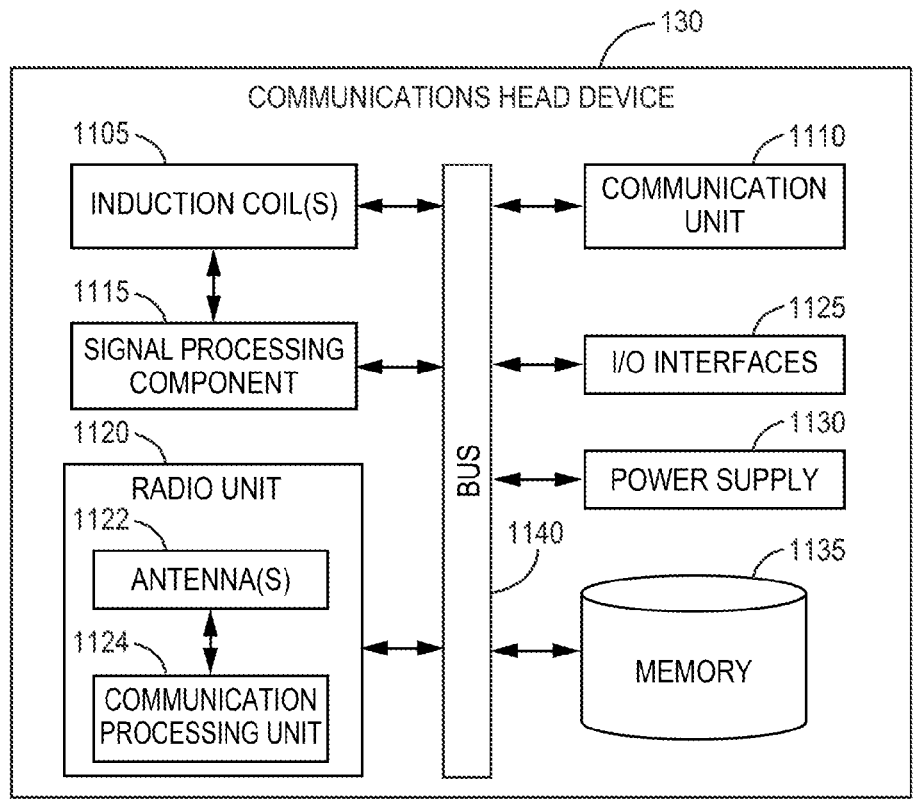
FIGS. 11-12 illustrate block diagrams of example, non-limiting communications head devices facilitating locating an IMD in accordance with one or more embodiments described herein.

FIG. 11 illustrates a block diagram of an example, non-limiting communications head device facilitating locating an IMD in accordance with one or more embodiments described herein. Repetitive description of like elements employed in other embodiments described herein is omitted for sake of brevity.

In the illustrated embodiment, the communications head device 130 can communicate wirelessly via inductive coupling with an IMD (e.g., the IMD 120) or other devices. To that end, as illustrated, the communications head device 130 includes one or more induction coils 1105 functionally coupled to a signal processing component 1115. At least one of the induction coil(s) 1105 can generate an alternating current by induction due to the presence of an alternating magnetic field generated at the IMD, for example. The generated alternating current can be modulated according to a modulation of the alternating magnetic field. The signal processing component 1115 can receive the alternating current and can demodulate at least a portion thereof, thereby generating a signal that can convey information from the IMD, for example. The modulation and demodulation can be implemented according to a specific protocol for communication via inductive coupling.

The signal processing component 1115 can send a signal generated in response to an inductive current to a communication unit 1110, which can receive and process at least a portion of the signal. The communication unit 1110 also can supply information to the signal processing component 1115, which can modulate at least a portion of the information for transmission to a device inductively coupled to the communications head device 130. To that end, in one example, the signal processing component 1115 can apply an alternating current to at least one of the induction coils(s) 1105. The alternating current can be modulated in order to generate a modulated magnetic field and, thus, send information wirelessly to such a device. Therefore, the communication unit 1110 can transmit, receive, and/or exchange information with an IMD (e.g., the IMD 120) inductively coupled thereto. In one example, the communication unit 1110 can exchange messages (such as a probe message and a related response message) with the IMD in order to generate strength data representative or otherwise indicative of strength of communicative coupling between the communications head device 130 and the IMD.

As illustrated in the example embodiment of FIG. 11, the communications head device 130 also can include a radio unit 1120 that can permit or otherwise facilitate wireless communication with a remote device other than an IMD. For instance, as described herein, the communications head device 130 can communicate wirelessly with the device 140 described herein (as described with reference to FIGS. 9-10). As such, in one example, the radio unit 1120 can have an architecture and/or functionality that is similar to that of the radio unit 905. More specifically, the radio unit 1120 can include one or more antennas 1122 and a communication processing unit 1124. In order to send, receive, and/or exchange information via the radio unit 1120, the communication unit 1110 can process at least a portion of the information. More specifically, in one example, the communication unit 1110 can generate information to be sent to the remote device, and can send the information to the communication processing unit 1124 for modulation and encoding according to a certain radio technology protocol. The communication processing unit 1124 can send or otherwise provide the modulated and encoded information to one or more of the antenna(s) 1122, which propagate such information over the air interface. As described herein, the communications head device 130 can wirelessly send strength information (e.g., strength data and/or related unprocessed data) to the device 140 via the radio unit 1120.

In certain embodiments, the presence of the induction coils 1105 and/or the radio unit 1120 in the communications head device 130 can permit or otherwise facilitate communication (e.g., concurrent or otherwise) between the communications head device 130 and multiple IMDs within the body, where two or more of multiple IMDs can communicate according to different communications protocols, e.g., inductive communication and RF-based communication.

Further, in the example embodiment shown in FIG. 11, the communications head device 130 also includes one or more input/output (I/O) interfaces 1125. Furthermore, the communications head device 130 also includes a power supply 1130 that can energize one or more components of the communications head device 130 for operation thereof. The power supply 1130 can have an architecture and functionality similar to those of the power supply 925.

Figure 12:
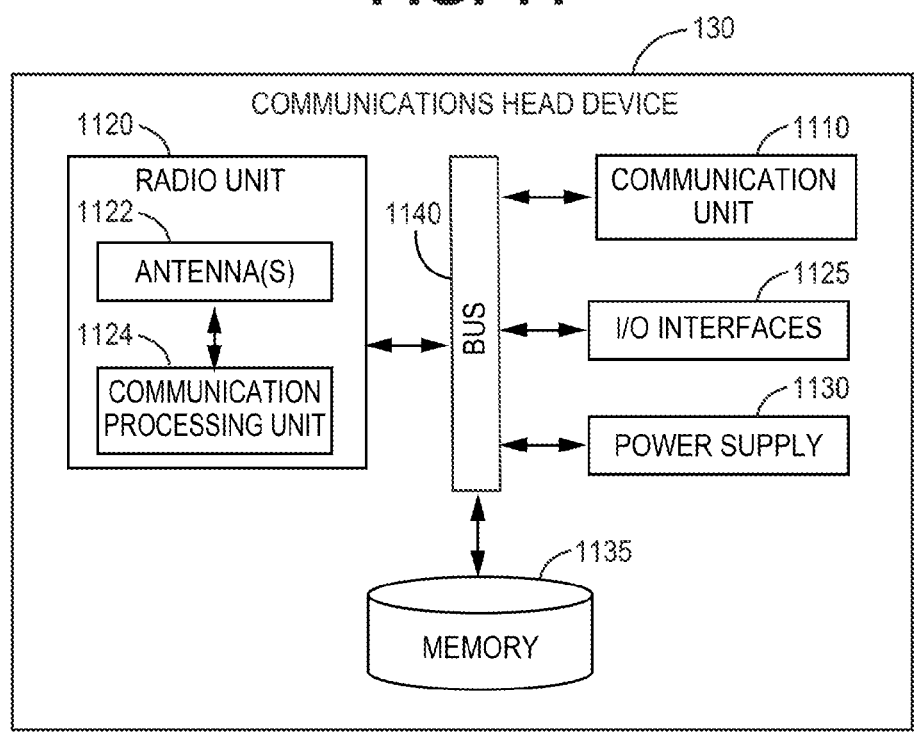

FIG. 12 illustrates a block diagram of an example, non-limiting communications head device facilitating locating an IMD in accordance with one or more embodiments described herein. Repetitive description of like elements employed in other embodiments described herein is omitted for sake of brevity. In the illustrated example embodiment, the communications head device 130 can utilize or otherwise leverage the radio unit 1120 to communicate wirelessly with an IMD, such as the IMD 120.

Figure 13:
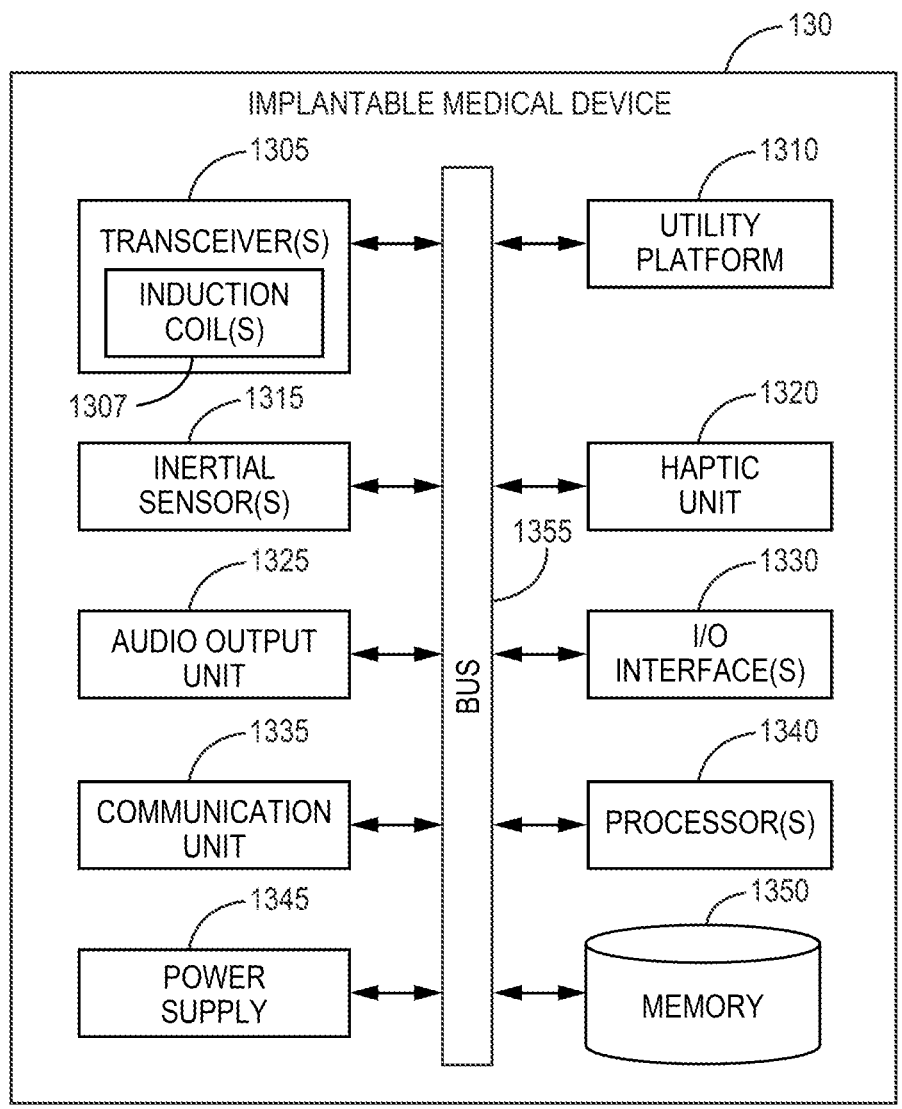
FIG. 13 illustrates a block diagram of an example, non-limiting IMD in accordance with one or more embodiments described herein.

FIG. 13 illustrates a block diagram of an example, non-limiting IMD in accordance with one or more embodiments described herein. Repetitive description of like elements employed in other embodiments described herein is omitted for sake of brevity.

As illustrated, the IMD 120 includes one or more transceivers 1305 that can permit sending, receiving, and/or exchanging information with a remote device, such as the communications head device 130 described herein. As illustrated, in an implementation in which inductive coupling is utilized for wireless communication, the transceiver(s) 1305 can include one or induction coils 1307 and a signal processing component. At least one of the induction coil(s) 1307 can generate an alternating current by induction due to the presence of an alternating magnetic field generated at a remote device, such as the communications head device 130. The generated alternating current can be modulated according to a modulation of the alternating magnetic field. One of the transceiver(s) 1305 or a component therein, can process the alternating current, thereby generating a signal that can convey information from the remote device. Similarly, a transceiver of the transceiver(s) 1305 or a component therein can generate another alternating current that can be applied to the induction coil(s) 1307 in order to generate another alternating magnetic field, which can induce alternative currents at the remote device. The alternating current generated by such a transceiver can be modulated in order to modulate the generated magnetic field. The modulation and demodulation utilized by the IMD 120 can be implemented according to a specific protocol for communication via inductive coupling. In an implementation in which wireless communication relies on propagated electromagnetic waves, the transceiver(s) 1305 can include one or more antennas and a communication processing unit (not shown). Notwithstanding the particular approach employed for wireless communication, a communication unit 1335 in the IMD 120 can process information to be sent to a remote device or information received there from.

As illustrated, the IMD 120 includes a utility platform 1310 that can provide or otherwise permit specific therapeutic functionality, such as drug delivery, neurological stimulation, cardiac defibrillation, heart pacemaking, or the like. Accordingly, the utility platform 1310 can include circuitry or components of various types. In certain implementations, the utility platform 1310 can utilize or otherwise leverage a haptic unit 1320 to provide a mechanical stimulus to the body in which the IMD 120 is implanted.

In addition, in the example embodiment 1300, the IMD 120 can include one or more inertial sensors 1315 that can determine characteristics of the motion and/or orientation of the IMD 120. The inertial sensor(s) 1325 can include a solid-state accelerometer and/or a gyroscope.

Further, the IMD 120 can include an audio output unit 1325 that can output audio signals in response to a specific operational condition of the IMD 120. The audio output unit 1325 can include a sound speaker, amplifiers, filters, and/or other circuitry configured to generate, output and/or otherwise process audio signals. Similarly, the haptic unit 1320 can provide a haptic signal (e.g., a vibration) in response to a specific operational condition or event. In various embodiments, the haptic unit 1320 can include an actuator or other type of electromechanical devices associated with vibration of the IMD 120. Furthermore, the IMD 120 also includes one or more input/output (I/O) interfaces 1330. At least one of the input interfaces of the I/O interface(s) can permit receiving information from an external device (e.g., communications head device 130), for example, and at least one output interface of the I/O interface(s) can permit sending or otherwise presenting information (e.g., history of activity of the IMD).

The IMD 120 also includes one or more processors 1340 that can provide or otherwise facilitate various functionality of the IMD 120. In one example, a processor of the processor(s) 1340 can control various functions of the IMD 120, such as transitioning from a power-save state to an active state, monitoring motion of the IMD 120 via, for example, via operation of the inertial sensor(s) 1315, generating and supplying a haptic signal via, for example, the haptic unit 1320 and/or communicating patient information. The processor(s) 1340 can also execute computer-executable instructions or other type of computer-accessible code (e.g., modules) retained in a memory 1350. The memory 1350 also can retain other types of information associated with operation of the IMD 120. The memory 1350 can be embodied in or can include one or more computer-readable storage devices.

A power supply 1345 can energize one or more components (e.g., a transceiver, a unit, a sensor, and/or an interface)

of the IMD 120 for operation thereof. The power supply 1345 can have similar structure and/or functionality to the power supply 925 described herein. In addition, two or more of the components included in the IMD 120 in the example embodiment can exchange information (e.g., data, metadata, and/or signaling) via a bus 1355. The bus 1355 can be embodied in or can include a system bus, a memory bus, a control bus, a combination thereof, or any other type of bus architecture for the exchange of information. The bus 1355 can permit wireless communication (e.g., optically switched communication), wireline communication, or a combination of both.

Figure 14:
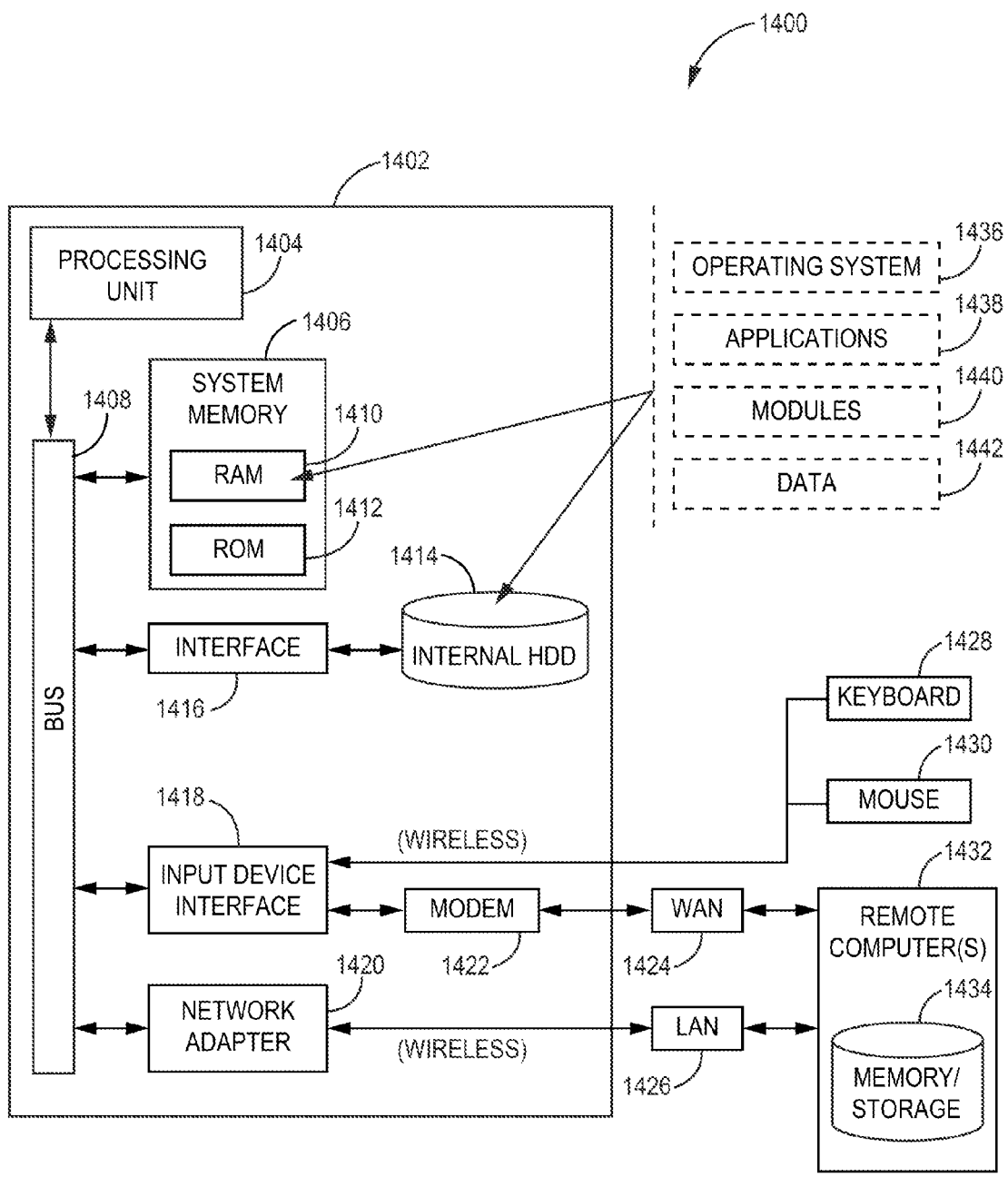
FIG. 14 illustrates a block diagram of an example, non-limiting computer operable to facilitate locating an IMD in accordance with one or more embodiments described herein.

FIG. 14 illustrates a block diagram of an example, non-limiting computer operable to facilitate locating an IMD in accordance with one or more embodiments described herein. For example, the computer 1402 can embody or constitute the IMD 120, the communications head device 130, the device 140, the server device 710, and/or the remote device 810. Repetitive description of like elements employed in other embodiments described herein is omitted for sake of brevity.

In order to provide additional context for one or more embodiments described herein, FIG. 14 and the following discussion are intended to provide a brief, general description of a suitable computing environment 1400 in which the one or more embodiments described herein can be implemented.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

Computing devices typically include a variety of media, which can include computer-readable storage media" and/or "communications media," which two terms are used herein differently from one another as follows. Computer-readable storage media or a computer-readable storage device can be any available storage media that can be accessed by the computer 1402 and includes both volatile and nonvolatile media, removable and non-removable media. By way of example, and not limitation, computer-readable storage media or a computer-readable storage device can be implemented in connection with any method or technology for storage of information such as computer-readable instructions, program modules, structured data or unstructured data. Tangible and/or non-transitory computer-readable storage media or a computer-readable storage device can include, but are not limited to, random access memory (RAM), read only memory (ROM), electrically erasable programmable read only memory (EEPROM), flash memory or other memory technology, compact disk read only memory (CD-ROM), digital versatile disk (DVD) or other optical disk storage, magnetic cassettes, magnetic tape, magnetic disk storage, other magnetic storage devices and/or other media that can be used to store desired information. Computer-readable storage media or computer-readable storage devices can be accessed by one or more local or remote computing devices, e.g., via access requests, queries or other data retrieval protocols, for a variety of operations with respect to the information stored by the medium.

In this regard, the term "tangible" herein as applied to storage, memory, computer-readable media, computer-readable storage media or computer-readable storage devices, is to be understood to exclude only propagating intangible signals per se as a modifier and does not relinquish coverage of all standard storage, memory, computer-readable media, computer-readable storage media or computer-readable storage devices that are not only propagating intangible signals per se.

In this regard, the term "non-transitory" herein as applied to storage, memory, computer-readable media or computer-readable storage media, is to be understood to exclude only propagating transitory signals per se as a modifier and does not relinquish coverage of all standard storage, memory, computer-readable media, computer-readable storage media or computer-readable storage devices that are not only propagating transitory signals per se.

Communications media can embody computer-readable instructions, data structures, program modules or other structured or unstructured data in a data signal such as a modulated data signal, e.g., a channel wave or other transport mechanism, and includes any information delivery or transport media. The term "modulated data signal" or signals refers to a signal that has one or more of the data signal's characteristics set or changed in such a manner as to encode information in one or more signals. By way of example, and not limitation, communication media include wired media, such as a wired network or direct-wired connection, and wireless media such as acoustic, RF, infrared (IR) and other wireless media.

With further reference to FIG. 14, the example operational environment 1400 for implementing one or more embodiments of the embodiments described herein includes computer 1402, processing unit 1404, system memory 1406 and system bus 1408. System bus 1408 couples system components including system memory 1406 to processing unit 1404. Processing unit 1404 can be any of various commercially available processors. Dual microprocessors and other multi-processor architectures can also be employed as processing unit 1404.

System bus 1408 can be any of several types of bus architecture that can further interconnect to a memory bus (with or without a memory controller), a peripheral bus, and a local bus using any of a variety of commercially available bus architectures. System memory 1406 includes RAM 1410 and ROM 1412. A basic input/output system (BIOS) can be stored in a non-volatile memory such as ROM, erasable programmable read only memory (EPROM), EEPROM, which BIOS contains the basic routines that help to transfer information between elements within computer 1402, such as during startup. RAM 1410 can also include a high-speed RAM such as static RAM for caching data.

Computer 1402 further includes internal hard disk drive (HDD) 1414 (e.g., Enhanced Integrated Drive Electronics (EIDE), Serial Advanced Technology Attachment (SATA)). HDD 1414 can be connected to system bus 1408 by a hard disk drive interface 1416. The drives and their associated computer-readable storage media provide nonvolatile storage of data, data structures, computer-executable instructions, and so forth. For computer 1402, the drives and storage media accommodate the storage of any data in a suitable digital format.

A number of program modules can be stored in the drives and RAM 1410, including operating system 1436, one or more application programs 1438, other program modules 1440 and program data 1442. All or portions of the operating system, applications, modules, and/or data can also be cached in RAM 1410. The systems and methods described herein can be implemented utilizing various commercially available operating systems or combinations of operating systems.

A mobile device can enter commands and information into computer 1402 through one or more wireless input devices, e.g., wireless keyboard 1428 and a pointing device, such as wireless mouse 1430. Other input devices (not shown) can include a smart phone, tablet, laptop, wand, wearable device or the like. These and other input devices are often connected to the processing unit 1404 through input device interface 1418 that can be coupled to system bus 1408, but can be connected by other interfaces, such as a parallel port, an IEEE serial port, a game port and/or a universal serial bus (USB) port.

Computer 1402 can operate in a networked environment using logical connections via wired and/or wireless communications to one or more remote devices, such as remote computer(s) 1432. Remote computer(s) 1432 can be embodied in or can include a workstation, a server computer, a router, a personal computer, portable computer, microprocessor-based entertainment appliance, a peer device or other common network node, and typically includes many or all of the elements described relative to computer 1402, although, for purposes of brevity, only memory/storage device 1434 is illustrated. The logical connections depicted include wired/wireless connectivity to a local area network (LAN) 1426 and/or larger networks, e.g., WAN 1424, as well as smaller PANs involving a few devices (e.g., at least two). LAN and WAN networking environments are commonplace in the home, offices (e.g., medical facility offices, hospital offices) and companies, and facilitate enterprise-wide computer networks, such as intranets, all of which can connect to a global communications network (e.g., the Internet).

When used in a LAN networking environment, computer 1402 can be connected to local network through a wired and/or wireless communication network interface or adapter 1420. Adapter 1420 can facilitate wired or wireless communication to LAN 1426, which can also include a wireless access point (AP) connected to the LAN 1426 for communicating with adapter 1420.

When used in a WAN networking environment, computer 1402 can include modem 1422 or can be connected to a communications server on WAN 1424 or has other means for establishing communications over WAN 1424, such as by way of the Internet. Modem 1422, which can be internal or external and a wired or wireless device, can be connected to the system bus 1408 via input device interface 1418. In a networked environment, program modules depicted relative to computer 1402 or portions thereof, can be stored in a remote memory/storage device. It will be appreciated that the network connections shown are example and other means of establishing a communications link between the computers can be used.

Computer 1402 can be operable to communicate with any wireless devices or entities operatively disposed in wireless communication via any number of protocols, including, but not limited to, NFC, Wi-Fi, ZigBee®, and/or BLUETOOTH® wireless protocols. Thus, the communication can be a defined structure as with a conventional network or simply an ad hoc communication between at least two devices.

NFC can allow point-to-point connection to an NFC-enabled device (e.g., NFC-enabled communications head device) in the NFC field of an IMD within the home or at any location. NFC technology can be facilitated using an NFC-enabled smart phone, tablet or other device that can be brought within 3-4 centimeters of an implanted NFC component. NFC typically provides a maximum data rate of 424 kilobits per second (Kbps), although data rates can range from 6.67 Kbps to 828 Kbps. NFC typically operates at the frequency of 13.56 megahertz (MHz). NFC technology communication is typically over a range not exceeding 0.2 meters (m) and setup time can be less than 0.1 seconds. Low power (e.g., 15 milliamperes (mAs)) reading of data can be performed by an NFC device.

Wi-Fi can allow connection to the Internet from a couch at home, a bed in a hotel room or a conference room at work, without wires. Wi-Fi is a wireless technology similar to that used in a cell phone that enables such devices, e.g., computers, to send and receive data indoors and out. Wi-Fi networks use radio technologies called IEEE 802.11 (a, b, g, n, etc.) to provide secure, reliable, fast wireless connectivity. A Wi-Fi network can be used to connect computers to each other, to the Internet, and to wired networks (which can use IEEE 802.3 or Ethernet). Wi-Fi networks operate in the unlicensed 2.4 and 5 GHz radio bands, at an 11 Mbps (802.11a) or 54 Mbps (802.11b) data rate, for example or with products that contain both bands (dual band), so the networks can provide real-world performance similar to the basic 10BaseT wired Ethernet networks used in many offices.

FIGS. 15-18 illustrate flow diagrams of example, non-limiting methods facilitating locating an IMD in accordance with one or more embodiments described herein. Repetitive description of like elements employed in other embodiments described herein is omitted for sake of brevity.

Figure 15:
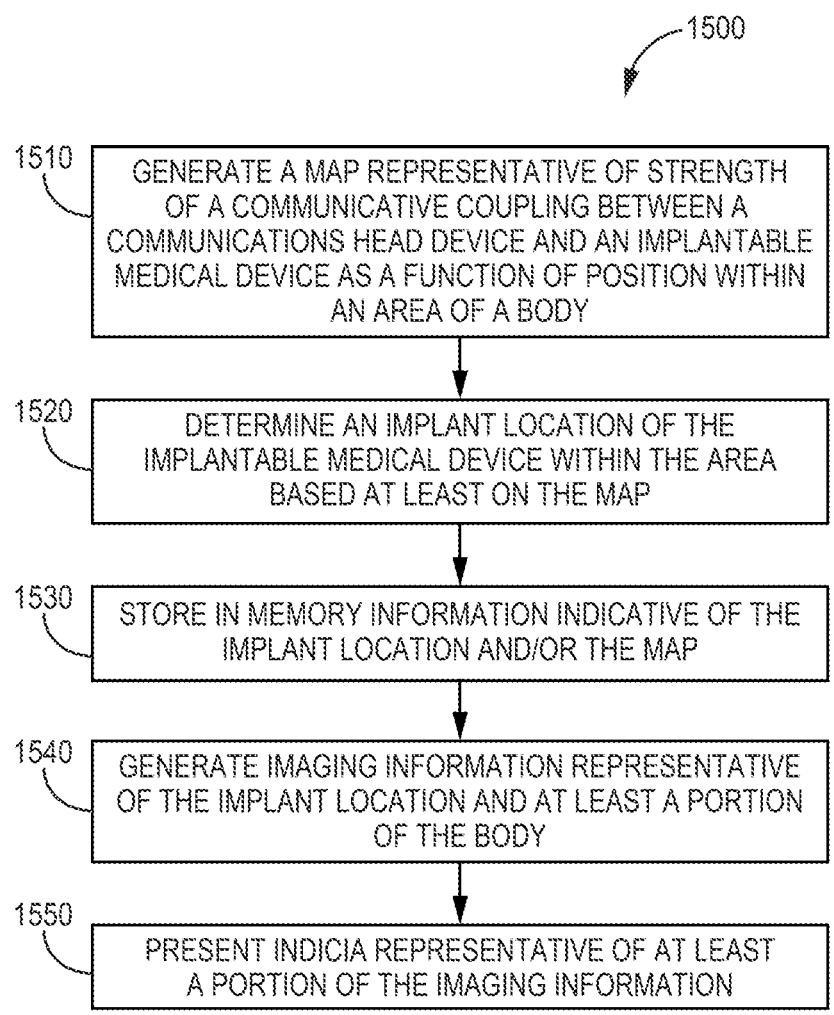
FIG. 15 illustrates a flow diagram of an example, non-limiting method facilitating locating an IMD in accordance with one or more embodiments described herein.

Turning first to FIG. 15, at 1510, the computing device can generate a map representative of strength of a communicative coupling between a communications head device (e.g., communications head device 130) and an IMD (e.g., IMD 120) as a function of position within an area of a body. For example, the map can be an electronic map representative of strength of the communicative couplings between the communications head device and the IMD as the communications head device is moved about on or in proximity to different locations of the body in which the IMD is implanted. In certain implementations, the map can be generated in accordance with the example method 1600 shown in FIG. 16 and described herein.

At 1520, the computing device can determine an implant location of the IMD based at least on the map in accordance with aspects described herein. At 1530, information indicative or otherwise representative of the implant location and/or the map can be stored in memory (e.g., one or more computer readable storage devices). At 1540, the computing device can generate imaging information representative or otherwise indicative of the implant location and at least a portion of the body. At 1550, the computing device can present indicia (e.g., indicia 194) representative of at least a portion of the imaging information. In certain embodiments, rather than the computing device presenting the indicia, the computing device can transmit a signal to another device (e.g., the remote device 810) to cause the other device to present such indicia. As such, the various functions described can be performed by a single device or distributed across a number of devices working collectively. All such embodiments are envisaged.

Humans are incapable of practicing all of the steps of method 1500, and therefore, ipso facto, the various aspects of method 1500 cannot be mere implementations of well-known or fundamental economic practices or human behavior nor as disembodied, mental or abstract steps or embodiments. For example, the method 1500 involves generation of an electronic map based on receipt of wireless or wireline signals indicative of the strength of a communicative coupling between a communications head device and an IMD. Method 1500 also involves display of electronic indicia representative of imaging information. In another example, several aspects of method 1500 involve the wireless reception of information over a wireless network, where the information generally is modulated and/or encoded according to a complex modulation and coding scheme. Thus, it is readily apparent that humans cannot perform such a reception of information via mental or abstract operations.

Figure 16:
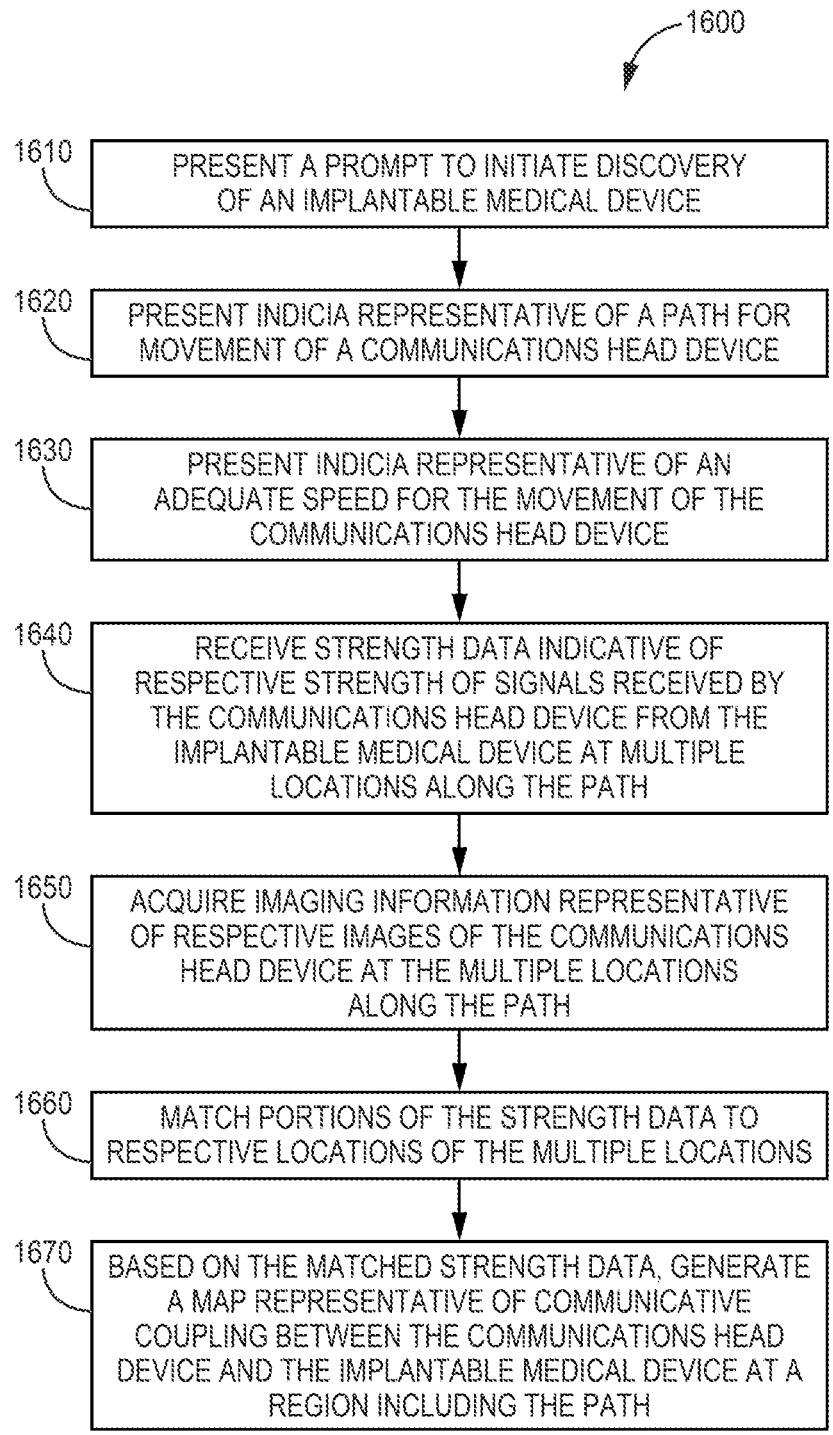
FIG. 16 illustrates a flow diagram of an example, non-limiting method facilitating generating a map of communicative coupling strength in accordance with one or more embodiments described herein.

FIG. 16 illustrates a flow diagram of an example, non-limiting method 1600 facilitating generating a map of communicative coupling strength in accordance with one or more embodiments described herein. Repetitive description of like elements employed in other embodiments described herein is omitted for sake of brevity.

At 1610, the computing device can present a prompt to initiate discovery of an IMD. For example, the prompt can initiate discovery of the location of the IMD within a body of a patient. In certain embodiments, rather than presenting the prompt, the computing device can cause another device (e.g., the remote device 810) to present the prompt.

In some embodiments, the IMD can be embodied in or can constitute the IMD 120 and can be implanted in a body. In some embodiments, in lieu of discovering the location of an IMD, the method 1600 can facilitate generating a map for discovery of the location of an implantable device. The implantable device can be communicatively coupled to and in close proximity to the IMD such that identification of the location of the implantable device can serve to provide a sufficient estimation of the identification of the location of the IMD, and corresponding communication between a communications head device and the IMD can commence based on placement of the communications head device at the location of the implantable device.

At 1620, the computing device can present indicia representative or otherwise indicative of a path (e.g., path 410 or path 510) for movement of a communications head device (e.g., communications head device 130). In certain embodiments, rather than presenting the indicia, the computing device can cause another device (e.g., the remote device 810) to present such indicia. For example, the computing device can generate a signal that can be received by the other device that instructs the other device, or otherwise causes the other device, to present indicia representative or otherwise indicative of the path. As such, the various functions described can be performed by a single device or distributed across a number of devices working collectively. All such embodiments are envisaged.

At 1630, the computing device can present indicia representative or otherwise indicative of an adequate speed for the movement of the communications head device. In certain embodiments, rather than presenting the indicia, the computing device can cause another device (e.g., the remote device 810) to present the indicia.

At 1640, the computing device can receive strength data (e.g., electronic strength data received over a wireless or wired communication channel) indicative or otherwise representative of respective strength of signals received by the communications head device from the IMD at multiple locations along the path. In certain embodiments, rather the receiving strength data, the computing device can receive raw data indicative or otherwise representative of an exchange of information between the communications head device and the IMD at multiple locations along the path. The raw data can be processed in order to generate strength data.

As such, in some embodiments, the communication device can process at least a portion of the received raw data in order to generate a metric representative of the strength of received by the communications head device from the IMD.

At 1650, the computing device can acquire imaging information (e.g., electronic imaging information) representative or otherwise indicative of respective images of the communications head device at the multiple locations along the path.

It should be appreciated that, in some embodiments, blocks 1630, 1640, and 1650 can be performed substantially concurrently as the communications head device traverses the path.

At 1660, the computing device can match or otherwise associate portions of the strength data to respective locations of the multiple locations along the path. At 1670, based on the matched strength data, the computing device can generate a map (e.g., electronic map) indicating the strength of communicative coupling between the communications head device and the IMD at a region of the body that includes the path.

Humans are incapable of practicing all of the actions of method 1600, and therefore, ipso facto, the various aspects of method 1600 cannot be mere implementations of well-known or fundamental economic practices or human activity nor as disembodied, mental or abstract operations or embodiments. For example, the method 1600 involves reception of strength data over a wireless channel, where the strength data is modulated and/or encoded according to a complex modulation and coding scheme. Thus, it is readily apparent that humans cannot perform the reception of the strength data via mental or abstract operations. Method 1600 also involves acquisition of electronic imaging information representative or otherwise indicative of respective images of the communications head device at the multiple locations along the path. In addition, the received strength data and the multiple locations can be matched to map strength of communicative coupling to position of the communications head device. Such a matching operation cannot be performed by a human as a mental or abstract step.

Figure 17:
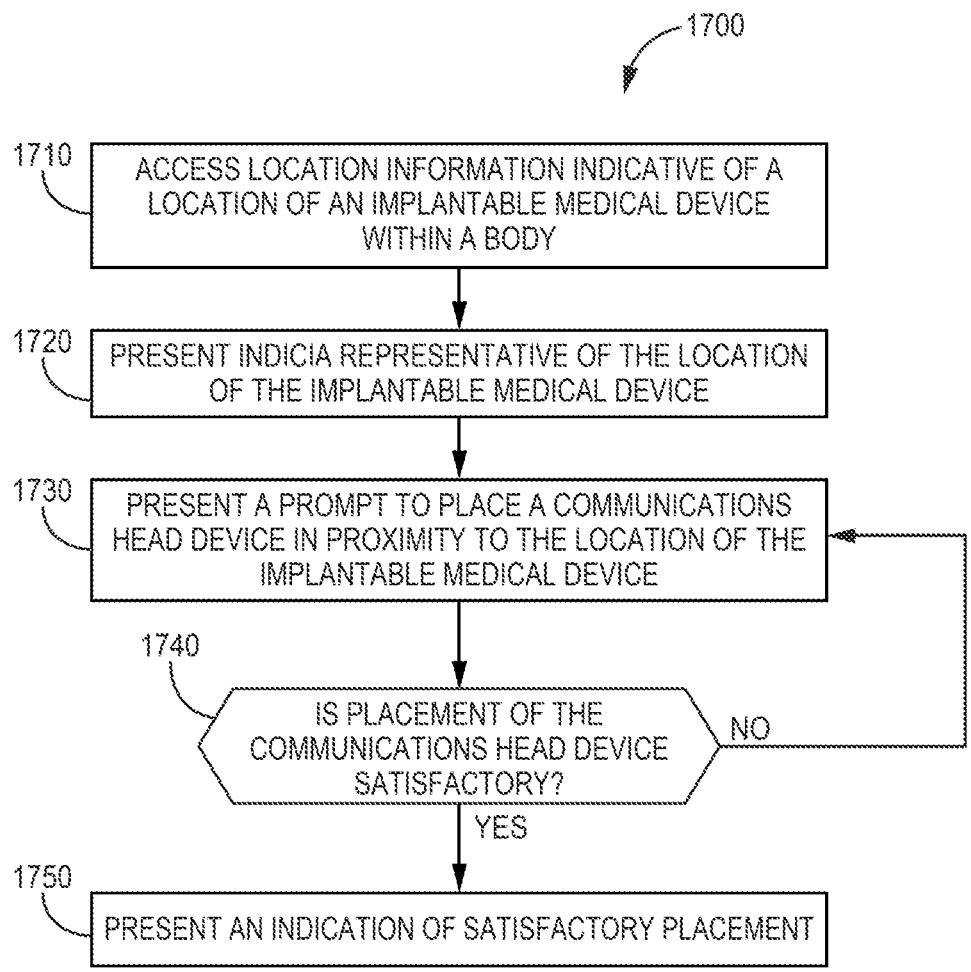
FIGS. 17-18 illustrate flow diagrams of example, non-limiting methods facilitating placement of a communications head device for communication with an IMD in accordance with one or more embodiments described herein.

FIG. 17 illustrates a flow diagram of an example, non-limiting method 1700 facilitating placement of a communications head device for communication with an IMD in accordance with one or more embodiments described herein. Repetitive description of like elements employed in other embodiments described herein is omitted for sake of brevity.

Similar to example methods 1500 and 1600, a computing device can implement the example method 1700 in its entirety or in part. At 1710, the computing device can access location information indicative or otherwise representative of a location of the IMD within a body (e.g., body of a patient). In certain embodiments, as described herein, the computing device can access the information from a computer-readable storage device integrated into the computing device or functionally coupled to the computing device. For example, the computing device can be embodied in the device 140 and can access the location information from a memory stored in the device 140, such as memory 950. In other embodiments, the computing device can access the location information from a server device (e.g., server device 710).

At 1720, the computing device can present indicia (e.g., output electronic indicia) representative of the location of the IMD. In addition or in other embodiments, rather than presenting the indicia, the computing device can cause another device (e.g., remote device 810) to present the indicia.

At 1730, the computing device can present a prompt to place the communications head device in proximity to the location of the IMD. Similarly to block 1720, in certain embodiments, the computing device can cause another device (e.g., remote device 810) to present such a prompt. For example, the computing device can generate an electronic signal that is transmitted to the remote device 810 to cause the remote device 810 to present a prompt. As such, the various functions described can be performed by a single device or distributed across a number of devices working collectively. All such embodiments are envisaged.

At 1740, the computing device can determine if the placement of the communications head device is satisfactory. For example, placement can be determined to be satisfactory if a signal strength between the communications head device and the IMD is greater than or approximately equal to a defined threshold (e.g., a defined threshold that may be called for to allow communication between the IMD and the communications head device, programming of the IMD by the communications head device or otherwise).

To that end, in one example, the computing device can receive strength information from the communications head device. The strength information can be representative of a magnitude of the communicative coupling strength between the communications head device and the IMD at a current placement of the communications head device. In addition, the computing device can compare such a magnitude with a specific threshold, and can ascertain that the placement of the communications head device is satisfactory when the magnitude is greater than or equal to the threshold. In response to ascertaining that the placement of the communications head device is not satisfactory, the flow of method 1700 can be directed to block 1730 in order to prompt replacement of the communications head device. In the alternative, in response to ascertaining that the placement of the communications head device is satisfactory, at 1750, the computing device can present an indication of satisfactory placement. In addition to or in certain embodiments, the computing device can cause another device, such as the communications head device or a remote device (e.g., remote device 810) to present the indication. For example, the computing device can cause the communications head device to output a haptic signal or an audio output signal if the placement is satisfactory.

Humans are incapable of practicing all of the steps of method 1700, and therefore, ipso facto, the various aspects of method 1700 cannot be mere implementations of well-known or fundamental economic practices or human activity nor as disembodied, mental or abstract operations or embodiments. For example, the method 1700 involves output of electronic indicia and/or transmission of one or more electronic signals from a computing device to a remote device.

For the methods shown in the flow diagrams of FIGS. 15-17, in one or more embodiments, the computing device can have or access computing resources that can implement (e.g., link, compile, and/or execute) the example method 1700 in its entirety or in part. In one embodiment, the method 1700 can be performed by the device 140. In another embodiment, the computing device can be embodied in or can constitute the server device 710. The computing resources can include, but are not limited to, processing resources (e.g., processor(s)), storage resources (e.g., computer-readable memory device(s)), and/or communications resources (e.g., a transceiver(s) and/or another type of network adapter).

Figure 18:
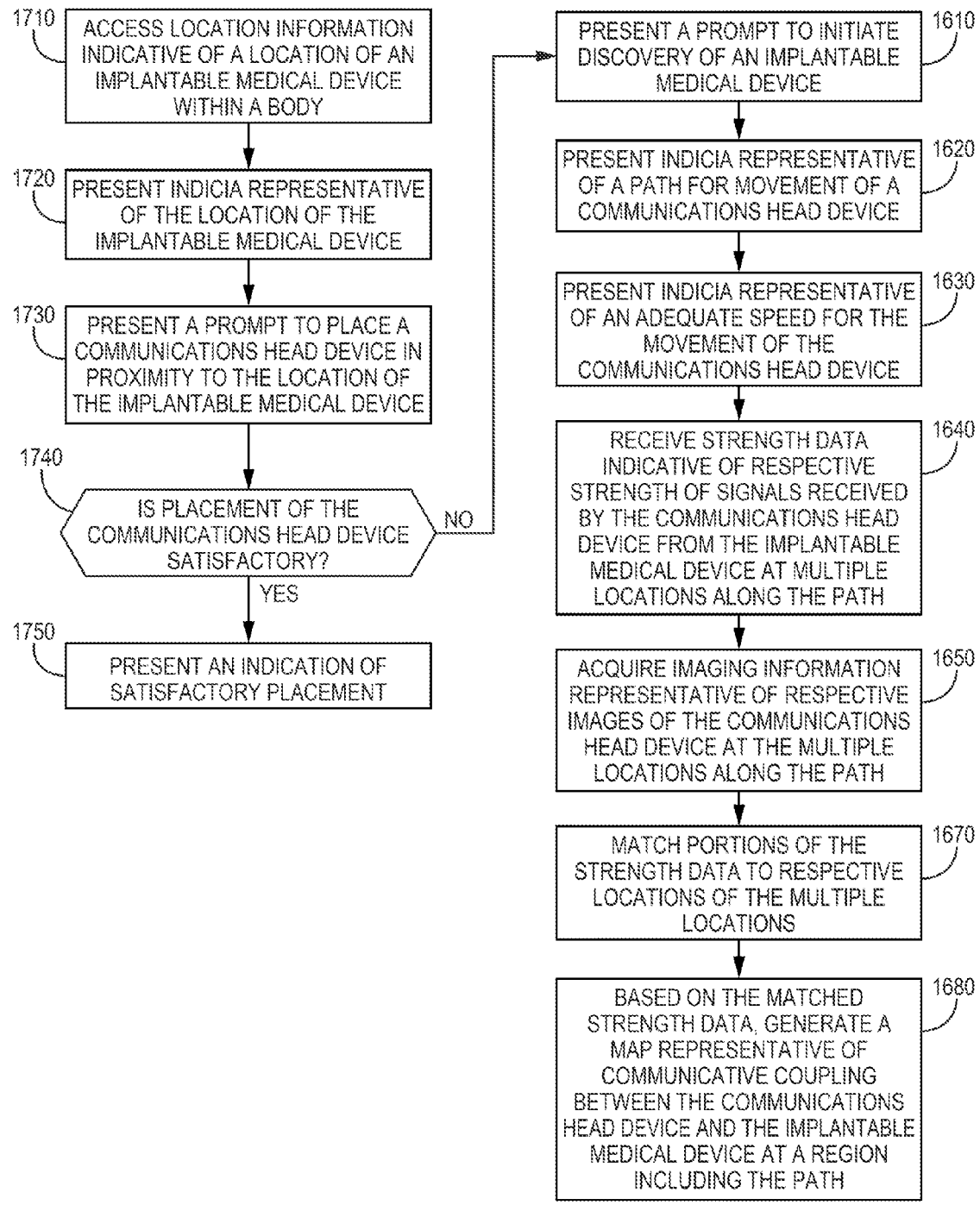

FIG. 18 illustrates a flow diagram of an example, non-limiting method 1800 facilitating placement of a communications head device for communication with an IMD in accordance with one or more embodiments described herein. Repetitive description of like elements employed in other embodiments described herein is omitted for sake of brevity.

The example method 1800 is similar to one or more aspects of example methods 1600 and 1700. For example, the operations of blocks 1710-1740 of FIG. 18 are those shown and/or described with reference to FIG. 17. In response to a determination, at block 1740, that the placement of the communications head device is not satisfactory, method 1800 can include various aspects of FIG. 16. By way of example, but not limitation, in response to a determination that the placement of the communications head device is not satisfactory, the operations of blocks 1610-1680 of FIG. 16 can be performed as part of method 1800.

Figure 19:
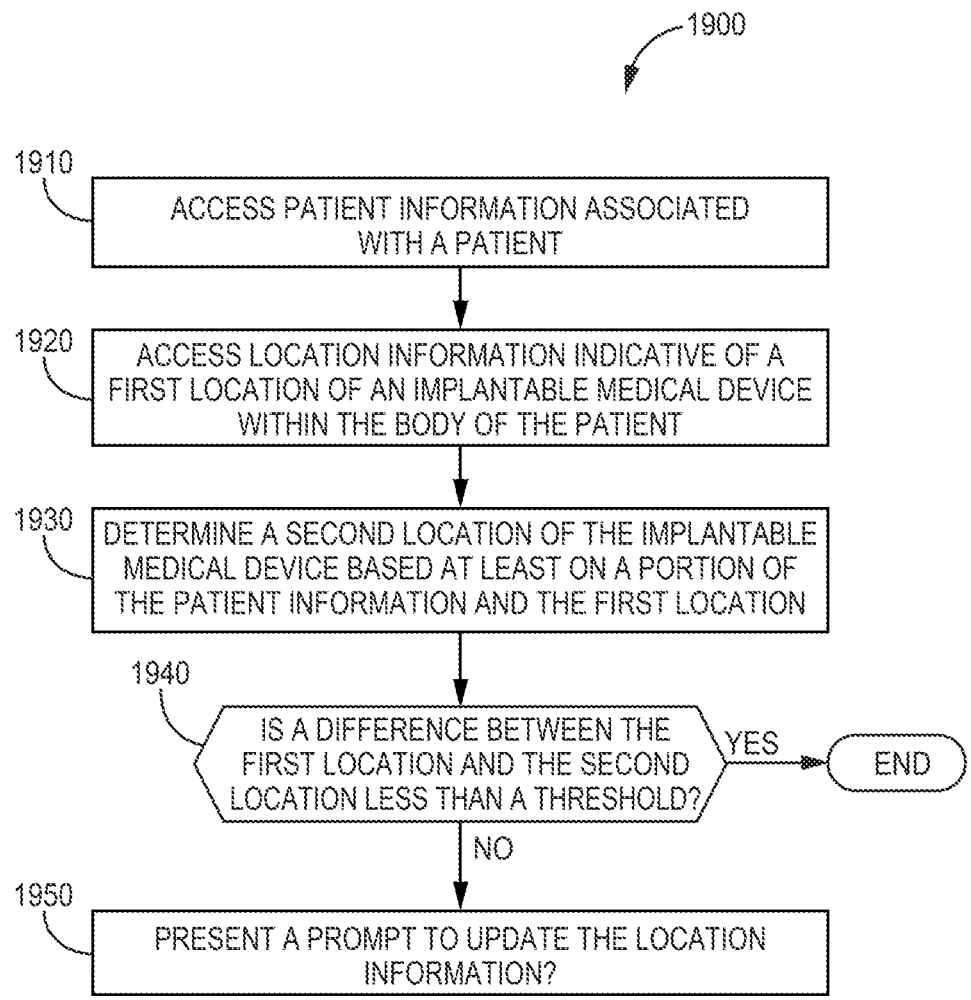
FIG. 19 illustrates a flow diagram of an example, non-limiting method facilitating monitoring placement of an IMD in accordance with one or more embodiments described herein.

FIG. 19 illustrates a flow diagram of an example, non-limiting method 1900 facilitating monitoring placement of an IMD in accordance with one or more embodiments described herein. Repetitive description of like elements employed in other embodiments described herein is omitted for sake of brevity.

Similar to other methods described herein, a computing device can implement the example method 1900 in its entirety or in part. At 1910, the computing device can access information associated with the patient. For example, the patient information can be stored electronic information and the computing device can access the patient information by communicating with a device storing the patient information over a wireless or wireline channel.

In certain embodiments, the computing device can access the patient information from a computer-readable storage device integrated into the computing device or functionally coupled thereto. For example, the computing device can be embodied in the device 140 and can access the patient information from a memory in the device 140, such as memory 950. In other embodiments, the computing device can access the patient information from a server device (e.g., server device 710).

By way of example, but not limitation, the patient information can include historical and/or contemporaneous information representative of the health and/or fitness of the patient. For example, the patient information can include demographic information (e.g., name, address information); biometric information (e.g., weight, heart rate, blood pressure, cholesterol level); information representative of health condition(s) of the patient (e.g., at-risk for hypertension; pre-hypertension, hypertension, at-risk for diabetes, pre-diabetic, diabetic; infectious diseases, auto-immune diseases, forms of cancer); information representative of therapies for the patient; and/or information indicative of the presence of or type of one or more IMD implanted within the body of the patient. In some embodiments, the patient information can include information such as the date or other indicator of time period during which an IMD was previously located via one or more methods described herein. In some embodiments, the patient information can include information indicative of the previously-estimated location of the IMD via one or more methods described herein (e.g., the IMD can have been determined to be a particular distance from the shoulder, a particular distance to either side of a body part or the like).

At 1920, the computing device can access location information indicative or otherwise representative of a first location of the IMD within the body of the patient. Similar to access of the patient information at 1910, in one or more embodiments, the computing device can access the location information from a computer-readable storage device integrated into the computing device or functionally coupled to the computing device. For instance, the computing device can be embodied in the device 140 and can access the location information from a memory therein, such as memory 950 or the memory 1010. In other embodiments, the computing device can access the location information from a server device (e.g., server device 710).

At 1930, the computing device can determine a second location of the IMD based at least on a portion of the patient information and the first location. In one implementation, determining the second location can include predicting a current location of the IMD based on a change in the patient's weight, and configuring the predicted current location as the second location. It should be recognized that the current location can be predicted based on other types of changes related to the patient's health or fitness. For instance, the current location can be predicted based on changes in the shape of the patient's body due to pregnancy or degenerative diseases, such as osteoporosis or amyotrophic lateral sclerosis (ALS).

At 1940, the computing device can determine if a difference between the second location and the first location is less than a threshold. In response to ascertaining that the difference is less than the threshold, the computing device can terminate the method 1900. In the alternative, in response to ascertaining that the difference is not less than the threshold, at 1950, the computing device can present a prompt to update the location information. In addition to or in other embodiments, the computing device can cause another computing device to present such a prompt.

Humans are incapable of practicing all of the action in method 1900, and therefore, ipso facto, the various aspects of method 1900 cannot be mere implementations of well-known or fundamental economic practices or human behavior nor as disembodied, mental or abstract operations or embodiments. For example, the method 1900 involves accessing and/or processing of electronic location information and/or electronic patient information over a network. As described herein, it would be appreciated that accessing such information can include, for example, collecting rich, complex digital information from a register or other memory element within a computer readable storage device that can be remotely located. In addition, processing of such information can include performing a substantial number of operations on digital information, which includes transmission and reception of electric signals associated with operation of electronic devices, such as gates, clocks, and the like.

Figure 20:
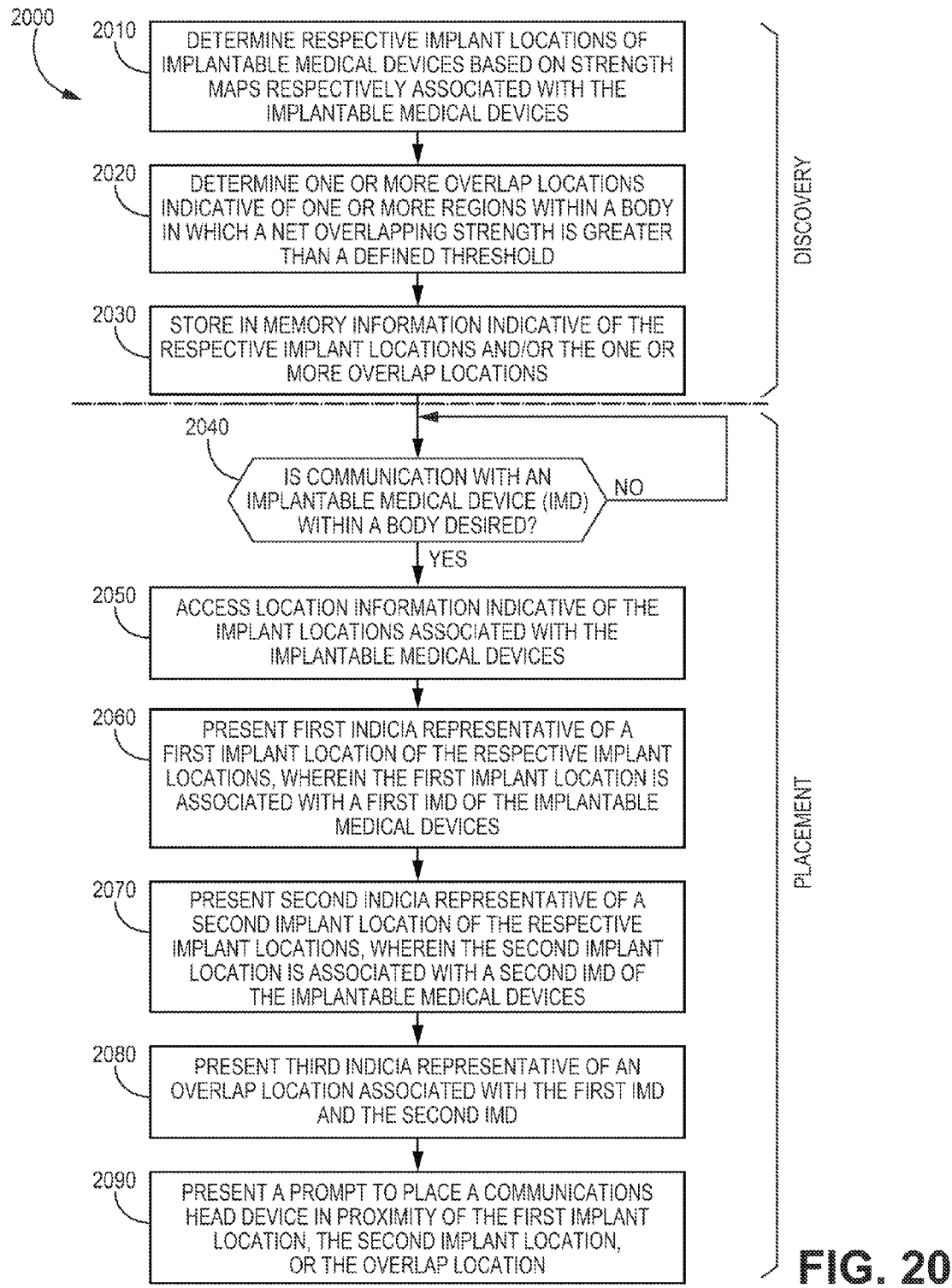
FIG. 20 illustrates a flow diagram of an example, non-limiting method facilitating locating one or more IMDs implanted within a single body in accordance with one or more embodiments described herein.
Figure 21:
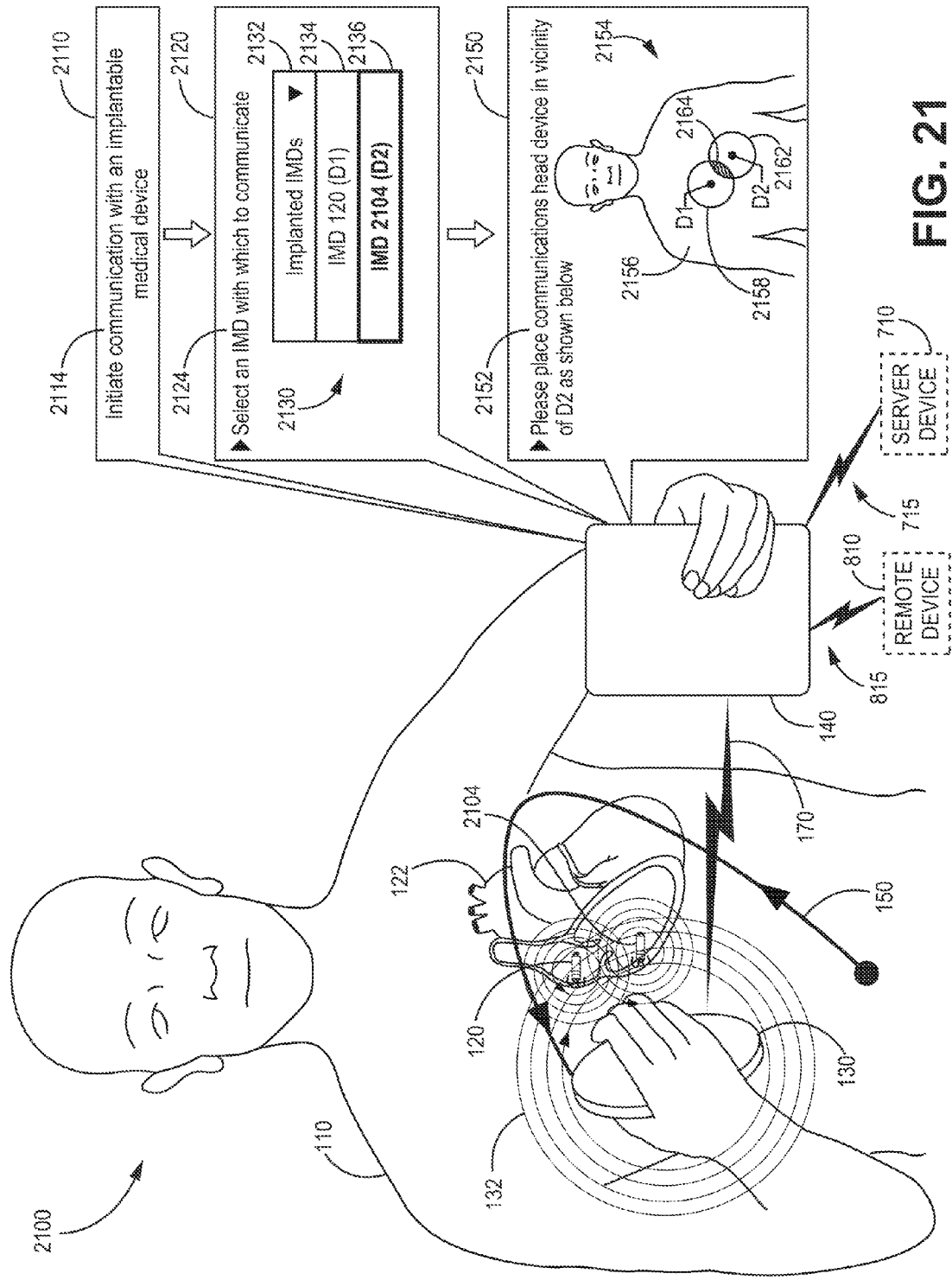
FIG. 21 illustrates a schematic diagram of an example, non-limiting medical device locating system facilitating locating one or more IMDs implanted with a single body in accordance with one or more embodiments described herein.

As described herein, embodiments described herein can permit or otherwise facilitate locating multiple IMDs within a body. Locating such devices (e.g., implantable therapeutic devices and/or implantable monitoring devices) can permit or otherwise facilitate placement of a communications head device (e.g., communications head device 130) for communication with a located IMD. More specifically, yet not exclusively, FIG. 20 illustrates a flow diagram of an example, non-limiting method facilitating locating one or more IMDs implanted within a single body in accordance with one or more embodiments described herein. Similar to other methods disclosed herein, one or more computing devices can implement the example method 2000 in its entirety or in part. FIG. 21 illustrates a schematic diagram of an example, non-limiting medical device locating system facilitating locating one or more IMDs implanted with a single body in accordance with one or more embodiments described herein. Repetitive description of like elements employed in other embodiments described herein is omitted for sake of brevity.

With reference to FIG. 20, at 2010, a computing device can determine respective implant locations of IMDs based on strength maps respectively associated with the IMDs. A first implant location can be determined in association with a first IMD and a second implant location can be determined in association with a second IMD. Implant locations for any number of IMDs can be determined in various embodiments. Accordingly, in certain embodiments, block 2010 can be implemented as an iterative implementation of example method 1500. For example, the computing device can be embodied in or can constitute the device 140, which can utilize or otherwise leverage a strength map in order to determine an implant location as described herein. As another example, the computing device can be embodied in or can constitute a server device (e.g., server device 710), which can utilize or otherwise leverage a strength map in order to determine an implant location as described herein.

At 2020, the computing device can determine one or more overlap locations indicative of one or more regions within a body in which a net overlapping strength is greater than a defined threshold.

For example, the net overlapping strength can result from overlapping signals originating from two or more of the IMDs and received by a communications head device, which can communicate with each of the two or more IMDs. In one embodiment, the computing device, e.g., device 140 or server device 710, can generate estimates of the one or more overlap locations. In another embodiment, in order to determine the one or more overlap locations, the computing device can receive information indicative of the one or more overlap locations from a second computing device (e.g., server device 710) and can generate the estimates of the one or more overlap locations.

At 2030, the computing device (e.g., device 140) and/or a remote computing device (e.g., remote device 810) can store in memory information indicative of the respective implant locations and/or the one or more overlap locations.

It should be appreciated that, collectively, blocks 2010 through 2030 can embody a discovery process in which multiple IMDs implanted in a body can be located, and the spatial dependence of the strength of the communicative coupling between each IMD and the communications head device can be established.

As exemplified in method 2000, subsequent to the discovery process, the computing device (e.g., device 140) can determine, at 2040, if communication with an IMD within the body is desired. For example, communication with an IMD can be desired immediately after locating the IMD and/or communication with an IMD can be desired after a period of time has elapsed since the collection of strength information and generation of the strength maps. As such, in some embodiments, the strength maps can be retrieved from a memory to facilitate the placement phase of method 2000.

In certain embodiments, a determination as to whether communication with an IMD is desired can be based on a trigger signal indicative or otherwise representative of a directive to initiate communication between the communications head device 130 and the IMD. In one example, the trigger signal can be received by the computing device from the communications head device.

In addition or in another example, the trigger signal can be generated by or received at the computing device. To that end, in some embodiments, input information can be received at the computing device and, in response, the trigger signal is generated. For instance, the input information can be received via an input interface (e.g., a display device with a touch screen or an audio input unit) of the computing device in response to a prompt to initiate communication, which can be displayed by the computing device.

More specifically, by way of example, in the system shown in FIG. 21, the computing device 140 can display a user interface 2110 including selectable indicia 2114 that conveys a prompt to initiate communication with an IMD within the body 110. While a specific message is illustrated in connection with the selectable indicia 2114, the embodiments described herein are not so limited and other messages can be presented. In response to selection of the indicia 2114, the device 140 can generate such a trigger signal. Similar to other selectable indicia described herein, the selectable indicia 2114 can be selected, for example, via touch (such as a tap or a pressure swipe) or other types of device-user interactions, including an utterance or a speech command or motion of the device 140.

With further reference to FIG. 20, in response to a determination at 2040 that communication with an IMD is not desired, in one embodiment, the computing device can continue monitoring for such a trigger signal indicating communication with an IMD is desired. In the alternative, in response to a determination that communication with an IMD is desired, at block 2050, the computing device (e.g., device 140 or server device 710) can access location information indicative of the implant locations associated with the IMDs discovered at block 2010. In some embodiments, the computing device can access location information for one of the implant locations associated with the IMDs. For example, the selected implant location can be that which may have been indicated to the computing device as the IMD of interest during a previous instance of initiating IMD communication, an implant location that has been indicated to be of interest more than a defined number of times or the like.

It can be appreciated that the computing device can access such information from the memory discussed with reference to 2030. In certain embodiments, in addition to accessing the implant location, the computing device can identify the IMDs (via device identifiers, for example) for which the implant location is accessed. Further to such identification, the computing device can present a prompt to select at least one of the identified IMDs.

As an illustration, in the example system shown in FIG. 21, the device 140 can display a user interface 2120 that can be generated based on a determination that communication with an IMD is desired (and corresponding input has been received in response to the indicia 2114). As such, user interface 2120 can be displayed as a result of an input to the device 140 at user interface 2110.

The indicia 2120 can include indicia 2124 conveying a prompt to select an IMD with which to communicate. In the example system shown, IMDs 120 and 2104 are implanted in the body 110 and available for selection. Therefore, the user interface 2120 can include indicia 2130 including selectable indicia 2132, which in response to selection, can present a device selection menu including selectable indicia 2134 representing selection of IMD 120 (labeled as D1) and indicia 2136 representing selection of IMD 2104 (labeled as D2).

Continuing with FIG. 20, at 2060, the computing device (e.g., device 140) can present first indicia representative of a first implant location of the implant locations, wherein the first implant location is associated with a first IMD of the IMDs. The implant locations can be those accessed at 2050. Similarly, at 2070, the computing device can present second indicia representative of a second implant location of the implant locations, wherein the second implant location is associated with a second IMD of the IMDs.

At 2080, the computing device can present third indicia representative of an overlap location associated with the first and second IMDs. As an illustration, in the example system shown in FIG. 21, the computing device can be embodied in or can constitute the device 140, and the first device can be embodied in or as the IMD 120 (e.g., an atrial leadless pacemaker) while the second device can be embodied in or as an IMD 2104 (e.g., a ventricular leadless pacemaker). In such a system, the device 140 can display a user interface 2150 that includes indicia 2154 including an image 2156 (e.g., a motion picture or a still picture, as described herein) combined with indicia 2158 representative of the implant location of a first device D1 (e.g., IMD 120), indicia 2162 representative of the implant location of a second device D2 (e.g., IMD 2104), and/or indicia 2164 representative of an overlap location at which the combined strength of communicative coupling between the communications head device 130 and the IMD 120, and the communicative coupling between the communications head device 130 and IMD 2104, is greater than a defined threshold.

With further reference to FIG. 20, at 2090, in various embodiments, the computing device (e.g., device 140) can present a prompt to place a communications head device in proximity of the first implant location, the second implant location, or the overlap location. Thus, the communications head device 130 can be placed in the region indicated by indicia 2158 for communication with IMD 120. The communications head device 130 can be placed in the region indicated by indicia 2162 for communication with IMD 2104. The communications head device 130 can be placed in the region indicated by indicia 2164 for concurrent communication with IMDs 120, 2104.

As an example, as illustrated in the system shown in FIG. 21, the user interface 2150 that is displayed by device 140 can include indicia 2152 that conveys a message to place the communications head device 130 in proximity to a predicted implant location for the IMD 2104, which is referred to as D2 in the user interfaces 2150.

It should be appreciated that, collectively, blocks 2040 through 2090 can embody a placement process in which a communications head device can be placed in proximity of one of numerous IMDs implanted in a body, in which such placement of the communications head device permits communication with one or more of the IMDs. Communication can occur individually with one of the IMDs or concurrently with two or more of the IMDs.

For purposes of simplicity of explanation, various methods disclosed herein are presented and described as a series of acts; however, it is to be understood and appreciated that the claimed and/or disclosed subject matter herein is not limited by the order of acts, as some acts may occur in different order and/or concurrently with other acts from that shown and described herein. It is noted that not all illustrated acts may be required to implement a described method in accordance with this disclosure. In addition, for example, one or more methods disclosed herein could alternatively be represented as a series of interrelated states or events, such as in a state diagram. Moreover, interaction diagram(s) or call flow(s) represent several of the example methods disclosed herein in accordance with the described subject matter; particularly in instances when disparate entities enact disparate portions of one or more of the several methods. Furthermore, two or more of the disclosed example methods can be implemented in combination, to accomplish one or more features or advantages described in this disclosure.

Methods disclosed throughout the specification and annexed drawings are capable of being stored on an article of manufacture (e.g., a removable volatile memory or nonvolatile memory) to facilitate transporting and transferring such methods to computers for execution, and thus implementation, by a processor, or for storage in a memory. In an aspect, one or more processors, such as processor(s) that implement the one or more methods described herein, can be employed to execute computer-executable instructions retained in a memory (volatile or non-volatile), or any computer-readable or machine-readable storage medium, to implement one or more of the method described herein. Such computer-executable instructions provide a computer-executable or machine-executable framework to implement the various methods described herein.

The embodiments of devices described herein can employ artificial intelligence (AI) to facilitate automating one or more features described herein. The embodiments (e.g., in connection with automatically identifying acquired cell sites that provide a maximum value/benefit after addition to an existing communication network) can employ various AI-based schemes for carrying out one or more embodiments thereof. Moreover, the classifier can be employed to determine a ranking or priority of each cell site of an acquired network. A classifier is a function that maps an input attribute vector, x=(x1, x2, x3, x4, ... , xn), to a confidence that the input belongs to a class, that is, f(x)=confidence (class). Such classification can employ a probabilistic and/or statistical-based analysis (e.g., factoring into the analysis utilities and costs) to prognose or infer an action that a mobile device desires to be automatically performed. A support vector machine (SVM) is an example of a classifier that can be employed. The SVM operates by finding a hypersurface in the space of possible inputs, which the hypersurface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

As will be readily appreciated, one or more of the embodiments can employ classifiers that are explicitly trained (e.g., via a generic training data) as well as implicitly trained (e.g., via observing mobile device behavior, operator preferences, historical information, receiving extrinsic information). For example, SVMs can be configured via a learning or training phase within a classifier constructor and feature selection module. Thus, the classifier(s) can be used to automatically learn and perform a number of functions, including but not limited to determining according to a predetermined criteria which of the acquired cell sites will benefit a maximum number of subscribers and/or which of the acquired cell sites will add minimum value to the existing communication network coverage, etc.

As employed herein, the term "processor" can refer to substantially any computing processing unit or device including, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components or any combination thereof designed to perform the functions described herein. Processors can exploit nano-scale architectures such as, but not limited to, molecular and quantum-dot based transistors, switches and gates, in order to optimize space usage or enhance performance of mobile device equipment. A processor can also be implemented as a combination of computing processing units.

Memory disclosed herein can include volatile memory or nonvolatile memory or can include both volatile and nonvolatile memory. By way of illustration, and not limitation, nonvolatile memory can include ROM, programmable ROM (PROM), electrically programmable ROM (EPROM), electrically erasable PROM (EEPROM) or flash memory. Volatile memory can include RAM, which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). The memory (e.g., data storages, databases) of the embodiments is intended to include, without being limited to, these and any other suitable types of memory.

As used herein, terms such as "data storage," "database," and substantially any other information storage component relevant to operation and functionality of a component, refer to "memory components," or entities embodied in a "memory" or components including the memory. It will be appreciated that the memory components or computer-readable storage media, described herein can be either volatile memory or nonvolatile memory or can include both volatile and nonvolatile memory.

In addition, the terms "example" and "such as" are utilized herein to mean serving as an instance or illustration. Any embodiment or design described herein as an "example" or referred to in connection with a "such as" clause is not necessarily to be construed as preferred or advantageous over other embodiments or designs. Rather, use of the terms "example" or "such as" is intended to present concepts in a concrete fashion. The terms "first," "second," "third," and so forth, as used in the claims and description, unless otherwise clear by context, is for clarity only and doesn't necessarily indicate or imply any order in time.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in this specification and annexed drawings should generally be construed to mean "one or more" unless specified otherwise or clear from context to be directed to a singular form.

What has been described above includes examples of one or more embodiments of the disclosure. It is, of course, not possible to describe every conceivable combination of components or methodologies for purposes of describing these examples, and it can be recognized that many further combinations and permutations of the present embodiments are possible. Accordingly, the embodiments disclosed and/or claimed herein are intended to embrace all such alterations, modifications and variations that fall within the spirit and scope of the detailed description and the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A device, comprising:
   a memory that stores executable modules;
   a processor coupled to the memory and configured to execute the following executable modules stored in the memory:
      a map composition module configured to generate information indicative of a first electronic map, wherein the first electronic map is representative of respective strengths of communicative couplings between a communications head device and an implantable medical device within a body at multiple positions of the communications head device relative to the body and during a first time period;
      a location prediction module configured to estimate an implant location of the implantable medical device within the body based on the information indicative of the first electronic map; and
      a media composition module configured to generate imaging information representative of an estimated implant location and at least a portion of the body.

2. The device of claim 1, further comprising:
   a display device configured to display indicia representative of at least a portion of the imaging information.

3. The device of claim 2, wherein the indicia comprises media including one or more of a video segment, a photograph, or schematic image.

4. The device of claim 3, wherein the display device is further configured to display a prompt to place the communications head device in a defined position relative to the body.

5. The device of claim 1, wherein the location prediction module is further configured to determine a location within the first electronic map at which one of the strengths of the communicative couplings is indicative of a strength intensity greater than a defined threshold.

6. The device of claim 1, wherein the location prediction module is further configured to predict a location within the first electronic map at which one of the strengths of the communicative couplings is indicative of maximal strength intensity.

7. The device of claim 1, wherein the map composition module is further configured to generate information indicative of a second electronic map, wherein the second electronic map is representative of respective strengths of communicative couplings between the communications head device and the implantable medical device within the body at multiple second locations of the communications head device relative to the body and during a second defined time period.

8. The device of claim 7, wherein the map composition module is further configured to generate the information indicative of the second electronic map based on a change in a size of the body, a time interval that has elapsed between commencement of the first defined time period and commencement of the second defined time period, or a defined change in a strength of a communicative coupling at a defined location of the body relative to an initial strength of an initial communicative coupling at the defined location of the body as indicated in the first electronic map.

9. The device of claim 7, wherein the location prediction module is further configured to determine that the implantable medical device is located at a second implant location, and the map composition module is further configured to generate the information indicative of the second electronic map based on a determination that the implantable medical device is located at the second implant location.

10. The device of claim 1, wherein the executable modules further comprise an acquisition module configured to receive strength data indicative of respective strengths of signals received by the communications head device from the implantable medical device at multiple locations along a path on the body, and wherein the processor is further configured to execute the acquisition module.

11. The device of claim 10, wherein the acquisition module is further configured to receive second imaging information representative of respective images of the communications head device at the multiple locations.

12. The device of claim 11, wherein the device further comprises a camera configured to:
   image the communications head device and at least a portion of the body; and
   generate the second imaging information.

13. The device of claim 10, wherein the map composition module is further configured to match portions of the strength data to respective locations of the multiple locations.

14. The device of claim 1, wherein the device is at least one of a tablet computer or a smart phone.

15. A device, comprising:
   a display device configured to output first indicia representative of a location of an implantable medical device within an area of a body, wherein the location is determined based on information indicative of a map representative of respective strengths of communicative couplings between a communications head device and the implantable medical device at multiple positions of the communications head device;
   a media composition module configured to generate imaging information representative of an estimated implant location of the implantable medical device and at least a portion of the body;
   a memory that stores executable modules;
   a processor coupled to the memory and configured to execute the following executable modules stored in the memory:
      a placement monitor module configured to determine whether placement of the communications head device satisfies a coupling criterion between the communications head device and the implantable medical device; and
      an output interface configured to output a placement indication based on a determination that the placement of the communications head device satisfies the coupling criterion.

16. The device of claim 15, wherein the placement indication comprises at least one of an audio output signal, a haptic signal, or a video output signal indicative of a second indicia representative of the location of the implantable medical device.

17. The device of claim 15, wherein the placement monitor module is further configured to cause the device to transmit, to the communications head device, a signal to cause the communications head device to output a haptic signal or an audio output signal if the placement of the communications head device satisfies the coupling criterion.

18. The device of claim 15, wherein the placement monitor module is further configured to process at least one of first data or second data from the communications head device, wherein the first data comprises strength data representative of a strength of a signal received from the implantable medical device by the communications head device at a defined location, and wherein the second data comprises raw data received from the implantable medical device by the communications head device at the defined location.

19. The device of claim 18, wherein the executable modules comprise a map composition module configured to update the map based at least on the first data or a metric computed from the second data, and wherein the processor is further configured to execute the map composition module.

20. A computer-readable storage device storing instructions that, in response to execution, cause a device comprising a processor to perform operations comprising:
generating information representative of respective strengths of communicative couplings between a communications head device and an implantable medical device within a body at multiple positions of the communications head device;
determining an estimate of a location of the implantable medical device within the body based at least on the information; and
generating imaging information representative of the estimate of the location and at least a portion of the body.

21. The computer-readable storage device of claim 20, wherein the operations further comprise:
causing the device to display a visual representation of at least a portion of the imaging information.

22. The computer-readable storage device of claim 20, wherein the determining further comprises predicting a position associated with a portion of the information representative of maximal strength intensity.

23. The computer-readable storage device of claim 20, wherein the operations further comprise storing in memory at least one of the estimate of the location of the implantable device or a portion of the information representative of respective strengths of communicative couplings between the communications head device and the implantable medical device.

24. The computer-readable storage device of claim 23, wherein the first indication comprises at least one of an audio output signal or a haptic signal, or a video output signal indicative of a second indicia representative of the location of the implantable medical device.

25. The computer-readable storage device of claim 20, wherein the operations further comprise:
causing the device to display first indicia representative of a location of an implantable medical device within an area of a body, wherein the location is determined based on information indicative of a map representative of respective strengths of communicative couplings between a communications head device and the implantable medical device at one or more positions of the communications head device;
determining that placement of the communications head device satisfies a coupling criterion between the communications head device and the implantable medical device; and
in response to the determining, outputting a first indication that the placement of the communications head device satisfies the coupling criterion.

26. A system, comprising:
a communications head device configured to determine strength data indicative of communicative couplings between the communications head device and one or more implantable medical devices located within a body of a patient; and
a device communicatively coupled to the communications head device and configured to:
receive the strength data for the one or more implantable medical devices;
generate one or more respective electronic maps based on the strength data for the one or more implantable medical devices, wherein a first electronic map of the one or more respective electronic maps is associated with a first implantable medical device of the implantable medical devices and wherein a second electronic map of the one or more respective electronic maps is associated with a second implantable medical device of the implantable medical devices;
generate imaging information representative of at least one estimated implant location of the one or more respective implant locations of the one or more implantable medical devices and at least a portion of the body;
determine estimates of one or more respective implant locations of the one or more implantable medical devices within the body based at least on the one or more respective electronic maps; and
display media representative of the estimates of the one or more respective implant locations of the one or more implantable medical devices and at least the portion of the body.

27. The system of claim 26, wherein the device is further configured to:
display a prompt to instruct a user of the communications head device to place the communications head device in proximity of the first implantable medical device, the second implantable medical device or an overlap region associated with communication between the communications head device, the first implantable medical device and the second implantable medical device.

28. The system of claim 26, wherein the device is further configured to:
output an indication that placement of the communications head device satisfies a placement criterion indicative of identification of a communicative coupling of the communicative couplings satisfying a defined criterion.

29. The system of claim 26, further comprising:
at least one of the implantable medical devices, wherein the implantable medical devices are configured to exchange information with the communications head device to determine at least a portion of the strength data.

30. The system of claim 26, further comprising:
a server device communicatively coupled to the device and configured to at least one of store information about the patient or transmit information about the patient to the device.

* * * * *